United States Patent
Alemany et al.

(10) Patent No.: US 6,403,370 B1
(45) Date of Patent: *Jun. 11, 2002

(54) ONCOLYTIC/IMMUNOGENIC COMPLEMENTARY-ADENOVIRAL VECTOR SYSTEM

(75) Inventors: Ramon Alemany, Grayslake; Xiangming Fang; Wei-Wei Zhang, both of Libertyville, all of IL (US)

(73) Assignee: GenStar Therapeutics Corporation, San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/797,160

(22) Filed: Feb. 10, 1997

(51) Int. Cl.[7] ............................................. C12N 15/861
(52) U.S. Cl. ..................... 435/320.1; 435/455; 435/456; 435/457
(58) Field of Search .............................. 435/69.1, 172.1, 435/172.3, 320.1, 366, 369, 370, 455, 456, 457; 424/93.2, 93.6, 93.1

(56) References Cited

U.S. PATENT DOCUMENTS

| | | | | |
|---|---|---|---|---|
| 5,470,560 | A | | 11/1995 | Martin |
| 5,648,478 | A | | 7/1997 | Henderson et al. ......... 536/241 |
| 5,654,168 | A | | 8/1997 | Bujard et al. |
| 5,658,776 | A | | 8/1997 | Flotte et al. |
| 5,670,488 | A | | 9/1997 | Gregory et al. ................ 514/44 |
| 5,691,176 | A | | 11/1997 | Lebkwoski et al. |
| 5,698,443 | A | * | 12/1997 | Henderson et al. ...... 435/320.1 |
| 5,871,726 | A | | 2/1999 | Henderson et al. ......... 424/93.2 |
| 5,882,877 | A | * | 3/1999 | Gregory et al. .......... 435/320.1 |
| 5,919,676 | A | | 7/1999 | Graham et al. ............. 435/91.4 |
| 5,932,210 | A | | 8/1999 | Gregory et al. ............ 424/93.2 |
| 5,935,935 | A | | 8/1999 | Connelly et al. .............. 514/44 |
| 5,994,104 | A | * | 11/1999 | Anderson et al. ........ 435/69.52 |
| 5,994,128 | A | | 11/1999 | Fallaux et al. ............... 435/325 |
| 5,994,132 | A | | 11/1999 | Chamberlain et al. ...... 435/369 |
| 6,051,218 | A | | 8/2000 | McBride et al. .......... 424/93.21 |
| 6,140,087 | A | * | 10/2000 | Graham et al. .......... 435/91.42 |
| 6,156,497 | A | * | 12/2000 | Kaleko ............................ 435/5 |

FOREIGN PATENT DOCUMENTS

| | | |
|---|---|---|
| EP | 592836 | 4/1994 |
| WO | WO 93/05817 | 4/1993 |
| WO | WO 94/12649 | 6/1994 |
| WO | WO 94/18992 | 9/1994 |
| WO | WO 94/23582 | 10/1994 |
| WO | WO 94/28152 | 12/1994 |
| WO | WO 94/29471 | 12/1994 |
| WO | WO 95/02697 | 1/1995 |
| WO | WO 95/11984 | 5/1995 |
| WO | WO 95/23867 | 9/1995 |
| WO | WO 95/27071 | 10/1995 |
| WO | WO 95/34671 | 12/1995 |
| WO | WO 96/13597 | 5/1996 |
| WO | WO 96/14061 | 5/1996 |
| WO | WO 96/14875 | 5/1996 |
| WO | WO 96/17053 | 6/1996 |
| WO | WO 96/18418 | 6/1996 |
| WO | WO 96/33280 | 10/1996 |
| WO | WO 96/34969 | 11/1996 |
| WO | WO 97/01358 | 1/1997 |
| WO | WO 97/09441 | 3/1997 |
| WO | WO 97/45550 | 12/1997 |

OTHER PUBLICATIONS

Berkner, Current Topics in Microbiology and Immunology, vol. 158, pp. 39–66, 1992.*

Orkin et al., "Report and Recommendations of the Panel to Assess the NIH Investment in Research on Gene Therapy", Dec. 7, 1995.*

Tanaka et al., Cancer Research, vol. 56, pp. 1341–1345, Mar. 15, 1996.*

Siders et al., Cancer Research, vol. 56, pp. 5638–5646, Dec. 15, 1996.*

Zhang et al., PNAS, vol. 93, pp. 4513–4518, Apr. 1996.*

W. French Anderson, Nature, vol. 392, pp. 25–30, Apr. 30, 1998.*

Verma et al., Nature, vol. 389, pp. 239–242, Sep. 18, 1997.*

Thomas Shenk, Group C Adenoviruses as Vectors for Gene Therapy, Chapter 3, in Viral Vector 1995.*

Fallaux et al., (Jan. 1996), *Human Gene Therapy*, vol. 7, pp. 215–222.

Mitani et al., (Apr. 1995), *Proc. Natl. Acad. Sci.*, vol. 92, pp. 3854–3858.

Gage et al., (Sep. 1992), *Journal of Virology*, vol. 66, No. 9, pp. 5509–5515.

Anton et al., (Aug. 1995), *Journal of Virology*, vol. 69, No. 8, pp. 4600–4606.

Kanegae et al., (1995), *Nucleic Acid Research*, vol. 23, No. 19, pp. 3816–3821.

(List continued on next page.)

*Primary Examiner*—David Guzo
(74) *Attorney, Agent, or Firm*—McDonnell Boehnen Hulbert & Berghoff

(57) ABSTRACT

This invention encompasses a composition for killing target cells, such as tumor cells. The composition comprises a first and a second adenoviral vector that have complementary function and are mutually dependent on each other for replication in a target cell. One of said adenoviral vectors has a target cell-activated promoter or a functional deletion that controls and limits propagation of the adenoviral vectors in the target cells which directly or indirectly kills the target cells. One of the adenoviral vectors comprises a gene encoding a protein which is expressed in the target cells and can induce anticancer immune responses. The target cells may be hepatoma, breast cancer, melanoma, colon cancer, or prostate cancer cells, for example. The vectors of this invention may also be utilized to treat other diseases such as restenosis, in which case the target cell may be a vascular smooth muscle cell, for example.

4 Claims, 13 Drawing Sheets

OTHER PUBLICATIONS

Deuschle et al., (Apr. 1995), *Molecular and Cellular Biology,* vol. 15, No. 4, pp. 1907–1914.

Park et al., (Nov. 1996), *Proc. Natl. Acad. Sci.,* vol. 93, No. 24, Abstract.

Imler et al., (Jan. 1996), *Gene Therapy,* vol. 3, No. 1, Abstract.

Ikawa et al., (Nov. 1995), "A rapid and non–invasive selection of transgenic embryos before implantation using green fluorescent protein (GFP)." *FEBS Letters,* vol. 375, No. 1,2, pp. 125–128.

Weitzman et al., (Jun. 1994), "Adeno–associated virus (AAV) Rep proteins mediate complex formation between AAV DNA and its integration site in human DNA." *Proc. Natl. Acad. Sci. USA,* vol. 91, pp. 5808–5812.

Connelly et al., (Jun. 1, 1996) "Sustained Expression of Therapeutic Levels of Human Factor VII in Mice." *Blood.* vol. 87, No. 11, pp. 4671–4677.

Alemany, et al, "Complementation of helper–dependent adenoviral vectors: size effects and tiler fluctuations" (1997), Journal of Virological Methods, 68, 147–159.

Chroboczek, et al, "The Sequence of the Genome of Adenovirus Type 5 and Its Comparison with the Genome of Adenovirus Type 2", (1992), Virology 186, 280–285.

Goldman, et al, "Transfer of the CFTR Gene to the Lung of Nonhuman Primates with El–Deleted, E2a–Defective Recombinant Adenoviruses: A Preclinical Toxicology Study", (1995), Human Gene Therapy 6:839–851.

Gorziglia, Mario, et al "Elimination of both E1 and E2a from Adenovirus Vectors Further Improves Prospects for In Vivo Human Gene Therapy", (1996), Journal of Virology p. 4173–4178.

Huber, Brian E., et al "Retroviral–mediated gene therapy for the treatment of hepatocellular carcinoma: An inovative approach for cancer therapy", (1991), Proc. Natl. Acad. Sci USA, vol. 88, pp. 8039–8043.

Urano, Yoshio, et al "Tandem arrangement of the albumin and α–fetoprotein genes in the human genome", (1984), Gene, 32:255–261.

Wang, Qing, et al "Correction of a Delection Mutant by Gene Targeting with an Adenovirus Vector", (1993), Molecular and Cellular Biology, pp. 918–927.

Wu, Kou–Juey, et al, "The Transcription Factor HNF1 Acts with C/EBP α Novel Domain", (1994), The Journal of Biological Chemistry, vol. 269, pp. 1177–1182.

Zhou, Heshan, et al, "Development of a Complementing Cell Line and a System for Construction of Adenovirus Vectors with E1 and E2a Deleted", (1996), Journal of Virology, pp. 7030–7038.

Bett et al., (Oct. 1993), *Journal of Virology,* vol. 67, No. 10, pp. 5911–5921.

Bischoff et al., (Oct. 1996), *Science,* vol. 274, pp. 373–376.

Siders et al., (Dec. 1996), *Cancer Research,* vol. 56, pp. 5638–5646.

* cited by examiner

FIG. 3A

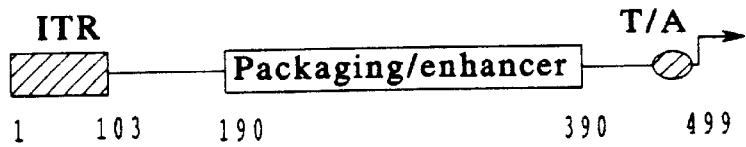

```
 ITR                                    T/A
 ▨──────[Packaging/enhancer]────────⬭──▶
 1    103  190                    390  499
```

FIG. 3B

```
    E1A Core          E2F               E1A Core
    ─────────▶        ─────             ─────────▶
GTGTACACAG GAAGTGACAA TTTTCGCGCG GTTTTAGGCG GATGTTGTAG
CACATGTGTC CTTCACTGTT AAAAGCGCGC CAAAATCCGC CTACAACATC
          200        210        220        230        240
     A I              A II                   E2F
                                             ─────
TAAATTTGGG CGTAACCGAG TAAGATTTGG CCATTTCGC GGGAAAACTG
ATTTAAACCC GCATTGGCTC ATTCTAAACC GGTAAAAGCG CCCTTTTGAC
          250        260        270        280        290
        E1A Core  A III        A IV
        ─────────▶
AATAAGAGGA AGTGAAATCT GAATAATTTT GTGTTACTCA TAGCGCGTAA
TTATTCTCCT TCACTTTAGA CTTATTAAAA CACAATGAGT ATCGCGCATT
          300        310        320        330        340
     A V               A VI     A VII
TATTTGTCTA GGGCCGCGGG GACTTTGACC GTTTACGTGG AGACTCGAAA
ATAAACAGAT CCCGGCGCCC CTGAAACTGG CAAATGCACC TCTGAGCGGG
          350        360        370        380        390
```

FIG. 3C

```
A repeat I      5'-GTAAATTTG-3'
A repeat II        GTAAGAATTTG
A repeat III       GTCAAATCTG
A repeat IV        ATAATTTTG
A repeat V         GTAATATTTG
A repeat VI        GGGACTTTG
A repeat VII       GACCGTTTA

CONSENSUS:      5'-GT-N_{3-4} TTTG-3'
```

FIG. 4
A. THE BASIC STRUCTURE OF THE SUPPLEMENTAL-AD VECTOR
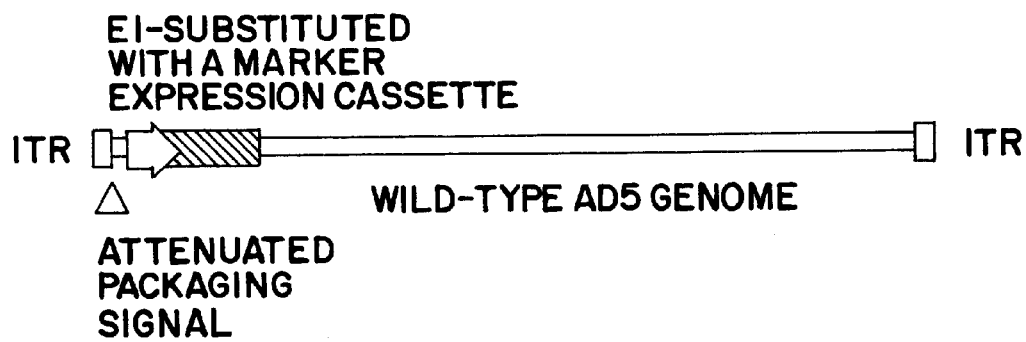
B. THE BASIC STRUCTURE OF THE CONTROLLED-AD VECTOR
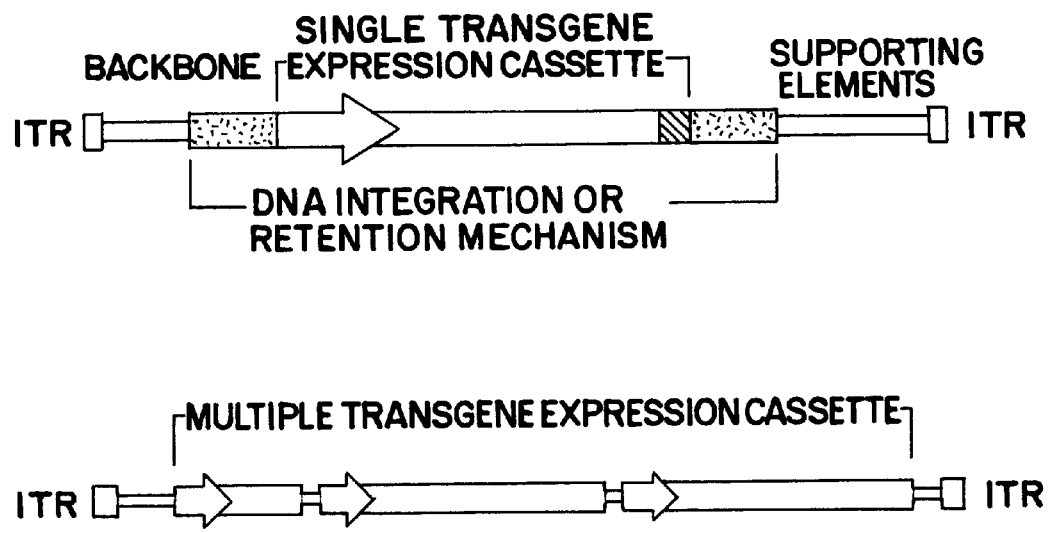

FIG. 5

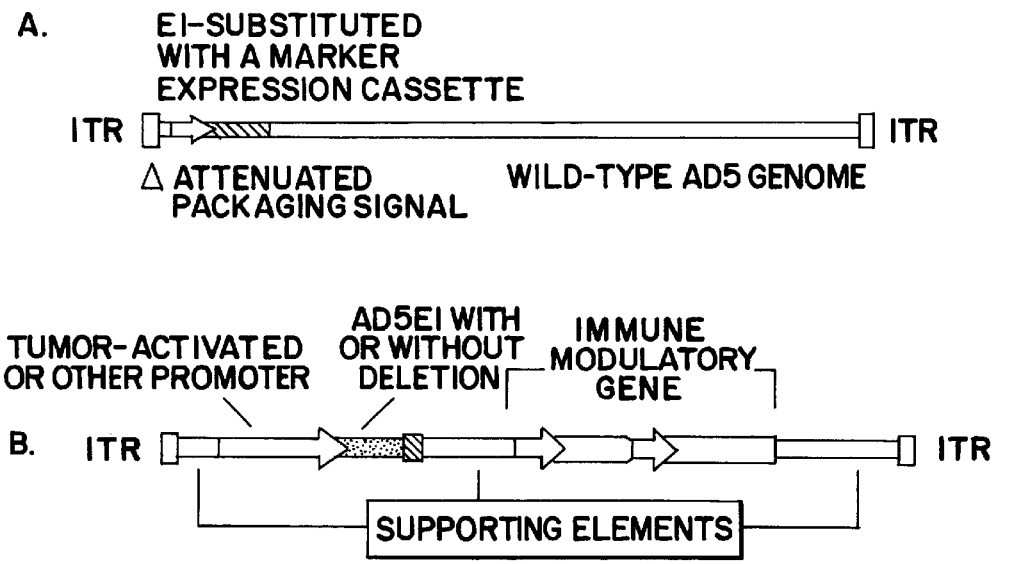

C. EXAMPLES OF TUMOR-ACTIVATED PROMOTERS AND IMMUNE MODULATORY GENES

| TUMOR-ACTIVATED PROMOTER | RELATED CANCER | IMMUNE MODULATORY GENES |
|---|---|---|
| α-FETAL PROTEIN PROMOTER | HEPATOMA | INTERFERON-γ |
| DF3-MUCIN ENHANCER | BREAST CANCER | B7 COSTIMULATORY FACTOR |
| TYROSINASE PROMOTER | MELANOMA | INTERLEUKINS |
| CEA PROMOTER | COLON CANCER | CHEMOKINES |
| PSA PROMOTER | PROSTATE CANCER | CYTOKINES |
| HI PARVOVIRUS PROMOTER | MULTIPLE CANCERS | TUMOR-SPECIFIC ANTIGENS |
| INDUCIBLE PROMOTER | MULTIPLE CANCERS | OTHER GENES |
| SYTHETIC PROMOTER | MULTIPLE CANCERS | |

FIG. 10

A. PACKAGING-ATTENUATED SUPPLEMENTAL-AD VECTOR WITH GENOME SUBSTITUTION

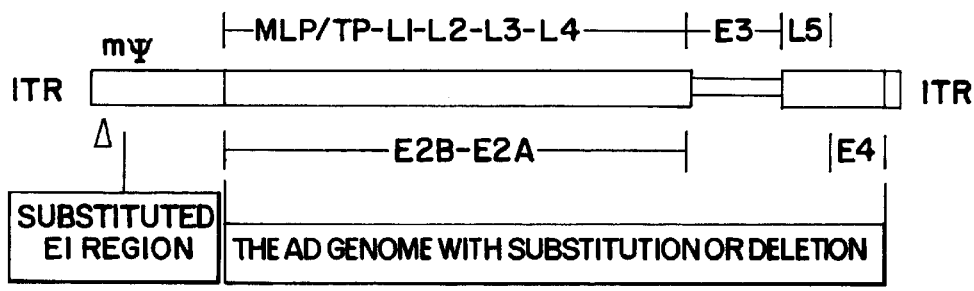

B. CONTROLLED-AD VECTOR THAT REQUIRES THE SUPPLEMENTAL-AD AND DELIVERS TRANSGENES

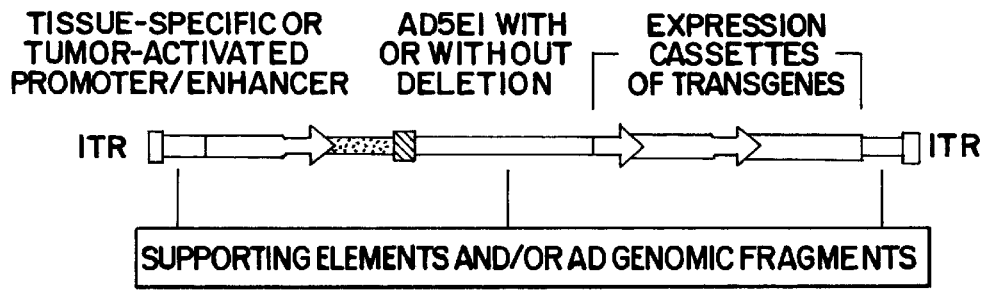

C. COMPLEMENTATION OF THE TWO VECTORS, TRANSGENE DELIVERY AND CONTROL

| ELEMENTS EQUIPPED | THE SUPPLEMENTAL-AD | THE CONTROLLED-AD |
|---|---|---|
| AD PACKAGING SIGNAL | MODIFIED/ATTENUATED | WILD-TYPE |
| AD E1 REGION | DELETED OR SUBSTITUTED | CARRIED/PARTIAL DELETED |
| AD E1 FUNCTION | DEPENDENT ON CONTROLLED-AD | SPECIFICALLY CONTROLLED |
| OTHER AD EARLY REGIONS | MAY BE SUBSTITUTED | MAY BE CARRIED |
| AD LATER REGION | MAY BE SUBSTITUTED | MAY BE CARRIED |
| TRANSGENE CARRIED | LIMITED AMOUNT | SINGLE AND/OR MULTIPLE |
| SUPPORTING ELEMENTS | NOT NECESSARY | SPECIALLY EQUIPPED |

SEQUENCE LISTING

<160> NUMBER OF SEQ ID NOS: 5

<210> SEQ ID NO 1
<211> LENGTH: 200
<212> TYPE: DNA
<213> ORGANISM: adenovirus type 5

<400> SEQUENCE: 1

```
gtgtacacag gaagtgacaa ttttcgcgcg gttttaggcg gatgttgtag t aaatttggg      60 cgtaaccgag taagatttgg ccattttcgc gggaaaactg aataagagga a gtgaaatct     120 gaataatttt gtgttactca tagcgcgtaa tatttgtcta gggccgcggg g actttgacc     180 gtttacgtgg agactcgaaa                                                  200
```

<210> SEQ ID NO 2
<211> LENGTH: 200
<212> TYPE: DNA
<213> ORGANISM: adenovirus type 5

<400> SEQUENCE: 2

```
cacatgtgtc cttcactgtt aaaagcgcgc caaaatccgc ctacaacatc a tttaaaccc      60 gcattggctc attctaaacc ggtaaaagcg ccctttttgac ttattctcct t cactttaga    120 cttattaaaa cacaatgagt atcgcgcatt ataaacagat cccggcgccc c tgaaactgg    180 caaatgcacc tctgagcggg                                                  200
```

<210> SEQ ID NO 3
<211> LENGTH: 10
<212> TYPE: DNA
<213> ORGANISM: adenovirus type 5

<400> SEQUENCE: 3

```
gtaagatttg                                                              10
```

<210> SEQ ID NO 4
<211> LENGTH: 10
<212> TYPE: DNA
<213> ORGANISM: adenovirus type 5

-continued

```
<400> SEQUENCE: 4
gtcaaatctg                                                              10

<210> SEQ ID NO 5
<211> LENGTH: 10
<212> TYPE: DNA
<213> ORGANISM: adenovirus type 5

<400> SEQUENCE: 5
gtaatatttg                                                              10
```

ONCOLYTIC/IMMUNOGENIC COMPLEMENTARY-ADENOVIRAL VECTOR SYSTEM

FIELD OF THE INVENTION

The invention is in the field of adenoviral vectors and their use in treating disease.

BACKGROUND OF THE INVENTION

Basic Adenoviral Vector Technology

Adenoviruses (Ad) consist of nonenveloped icosahedral (20 facets and 12 vertices) protein capsids with a diameter of 60–90 nm and inner DNA/protein cores (Horwitz, 1990). The outer capsid is composed of 252 capsomers arranged geometrically to form 240 hexons (12 hexons per facet) and 12 penton bases; the latter are located at each vertex from which protrude the antennalike fibers. This structure is responsible for attachment of Ad to cells during infection. Wild-type Ad contain 87% protein and 13% DNA and have a density of 1.34% g/ml in CsCl.

The double-stranded linear DNA genome of Ad is approximately 36 kb, and is conventionally divided into 100 map units (mu). Each end of the viral genome has a 100–150 bp repeated DNA sequence, called the inverted terminal repeats (ITR). The left end (194–385 bp) contains the signal for encapsidation (packaging signal). Both the ITRs and the packaging signal are cis-acting elements necessary for adenoviral DNA replication and packaging (Sussenbach, 1984; Philipson, 1984).

A simplified map of the adenovirus type 5 (Ad5) genome with a few key landmarks is diagrammed in FIG. 1 (Stratford-Perricaudet and Perricaudet, 1991; Graham and Prevec, 1991). The early (E) and late (L) regions of the genome contain several transcription units and are divided according to the onset of viral DNA replication. The E1 region (E1A and E1B) encodes proteins responsible for the regulation of transcription of the viral genome as well as a few cellular genes (Nevins, 1993). The expression of the E2 region (E2A and E2B) leads to the synthesis of the proteins needed for viral DNA replication (Pettersson and Roberts, 1986). The proteins from the E3 region prevent cytolysis by cytotoxic T cells and tumor necrosis factor (Wold and Gooding, 1991). The E4 proteins are involved in DNA replication, late gene expression and splicing, and host cell shut-off (Halbert et al, 1985). The products of the late genes, including the majority of the viral capsid proteins, are expressed after processing of a 20-kb primary transcript driven by the major late promoter (MLP) (Shaw and Ziff, 1980). The MLP (located at 16.8 mu) is particularly efficient during the late phase of infection, and the mRNAs issued from this promoter possess a 5' tripartite leader (TL) sequence, which increases the preference of the host cell for such transcripts as opposed to host cell mRNAs.

The use of Ad as vectors for expression of heterologous genes began soon after the observation of hybrids between Ad and simian virus 40 (SV40) during the 1960s. Since then, Ad vectors have gradually developed into one of the major viral vectors in the current field of gene therapy, because: (a) Ad have been widely studied and well characterized as a model system for eukaryotic gene regulation, which served as a solid base for vector development; (b) The vectors are easy to generate and manipulate; (c) Ad exhibits a broad host range in vitro and in vivo with high infectivity, including non-dividing cells; (d) Ad particles are relative stable and can be obtained in high titers, e.g., $10^{10}$–$10^{12}$ plaque-forming unit (PFU)/ml; (e) The life cycle of adenovirus does not require integration into the host cell genome, and, therefore, the foreign genes delivered by Ad vectors are expressed episomally, thus having low genotoxicity if applied in vivo; (f) Side effects have not been reported following vaccination of U. S. recruits with wild-type Ad, demonstrating their safety for in vivo gene transfer. Ad vectors have been successfully used in eukaryotic gene expression (Levrero et al, 1991; Ghosh-Choudhury, 186), vaccine development (Granhaus and Horwitz, 1992; Graham and Prevec, 1992), and gene transfer in animal models (Stratford-Perricaudet and Perricaudet, 1991; Stratford-Perricaudet et al, 1992; Rich et al, 1993). Experimental routes for administrating recombinant Ad to different tissues in vivo have included intratracheal instillation (Rosenfeld et al, 1992), muscle injection (Quantin et al, 1992), peripheral intravenous injection (Herz and Gerard, 1993), and stereotactic inoculation to brain (LaSalle et al, 1993). The initial Ad-mediated gene therapy trial in humans was the transfer of the cystic fibrosis transmembrane conductance regulator (CFTR) gene to lung tissues (Crystal et al, 1994).

Gene-Transfer Mediated Anticancer Immunity

One of the most effective current approaches to cancer gene therapy involves alteration of the tumor-host relationship and facilitation of recognition and destruction of malignant cells by the host immune system. In the tumor-bearing individual, a lack of an effective immune response may be due in part to either weak tumor cell antigenicity, lack of immune co-stimulation, or a tumor-specific immunosuppressive environment. Gene transfer of cytokines to tumor cells provides a strategy for augmentation of an effective anti-tumor immune response (Miller et al, 1994). In recent years, a number of cytokine genes have been isolated, cloned and characterized. Systemic administration of certain of these immunomodulators, such as IL-2, has resulted in an anti-tumor response. However, significant toxicity has accompanied the use of many of these biologics owing to the high concentrations needed to generate clinical effects. The combination of significant undesired effects and marginal therapeutic outcomes from systemic administration has stimulated efforts to genetically engineer tumor cells to produce the cytokines themselves (Rosenberg et al, 1989).

In animal models, gene-modified tumor cells have been used as vaccines to stimulate anti-tumor response (Miller et al, 1994; Dranoff and Mulligan, 1995). The appeal of tumor directed cytokine gene transfer is that the cytokine, produced locally, is immunologically more efficient and does not cause systemic toxicity. Tumor antigens expressed on neoplastic cells in combination with high local concentrations of cytokine(s), creates an immunological micro-environment virtually impossible to reproduce with exogenous cytokine administration. This immunological micro-environment created by such cytokine-producing tumor cells has been shown to result in generation of cytotoxic T lymphocytes. In a number of different animal models, cytokine-producing tumor cells have been shown to be effective in decreasing the tumorgenicity and increasing the expression of immunologically important molecules (Miller et al, 1994; Dranoff and Mulligan, 1995). The initial antitumor rejection appears to be accompanied by a nonspecific inflammatory response. However, rejection of cytokine secreting tumor cells has in most instances led to the generation of systemic, tumor specific immunity that is T cell-dependent.

In addition, new evidence indicates that co-stimulation of T cells by the co-stimulatory molecule B7 has both a positive and negative effect on T cell activation (Leach et al, 1996). Other co-stimulatory molecules for T cells such as ICAM-I, LFA-3 and VCAM-I have also been implicated in the induction of an anti-tumor response (Springer, 1990).

The most powerful of these co-stimulatory signals is provided by the interaction of CD28 on a T cell with either or both of its primary ligands, B7-1 (CD80) and B7-2 (CD86) on the surface of an antigen presenting cell (Lenschow et al, 1996). In a variety of model systems, tumor cells transfected with the B7 cDNA induced potent antitumor responses against both modified and unmodified tumor cells (Townsend and Allison, 1993)

It has long been known that both Class I and Class II MHC molecules are involved in the tumor antigen presentation, although different pathways are utilized by the two classes of molecules. Class I MHC has been shown to activate tumor-specific CTL in vitro. Early work on tumor vaccination included transfection of MHC class I genes and resulted in suppression of the tumor cells in tumorigenicity and/or metastasis in mouse models (Hui et al, 1984; Wallich et al, 1985) MHC class II genes were shown to be involved in activation of tumor-specific T-helper cells, and the introduction of Class II genes into tumor cells resulted in a decrease in the tumorigenicity and generated a systemic immune response against the parental tumor (Ostrand-Rosenberg, 1990). Despite these positive results, the relationship between levels of MHC expression and immunogenicity is inconsistent among tumor models. Researchers have recently begun to believe that the inconsistency is caused by other cofactors, such as the B7 co-stimulatory molecule, which affects the antigen presentation by MHC/peptide complexes.

Interferon gamma (IFN-γ) is a pleiotropic cytokine that, for example, activates macrophages and plays an important role in the inflammatory response (Billiau, 1996). This pleiotropic cytokine is also a potent inducer of MHC class I and class II antigens and thus is capable of enhancing immune responses (Wallach et al, 1982; Chen et al, 1986). Retroviral transduction of a cDNA encoding murine IFN-γ into a non-immunogenic murine sarcoma cell line that expresses low levels of MHC Class I only weakly induced upregulation of MHC class I antigen expression and generated anti-tumor CD8$^+$ TIL. Following tumor rejection, long-lasting protection from rechallenge with parental cells was induced (Nicholas et al, 1992). Moreover, innoculation of mice having micro-metastases with tumor cells producing large amounts of IFN-γ almost completely cured these mice by inducing CTL (Porgador et al, 1993). The cDNA for human IFN-γ has also been introduced into human renal cancer cells and melanoma cells (Gansbacher et al, 1992; Gastl et al, 1992). Renal cancer cells secreting IFN-γ showed increased expression of MHC class I antigen, $\mu$2-microglobulin, and intracellular adhesion molecule I, as well as induction of MHC class II antigen expression. However, tumor formation by a human renal cancer cell line transplanted into nu/nu mice was not affected by IFN-γ secretion, whereas IL-2 production inhibited growth of the tumor.

Many other cytokines, chemokines, and intercrines have been shown to play several different roles in eliciting anti-tumor immunity (Allione et al., 1994; Plata-Salaman and Borkoski, 1994; Zhang and Fang, 1995). Further studies using gene transfer of multiple cytokine or immuno-stimulatory genes have obtained induction of stronger anti-cancer immunity (Vagliani et al, 1996). The cytokine or immune modulatory genes have also been used in combination with other gene transfer for development of more effective approaches to gene therapy of cancer (Zhang and Fang, 1995).

Genetically-Engineered Virus Therapy of Cancer

Since the 1920s, viruses have been utilized to induce oncolysis (See review article: Sinkovics and Horvath, 1993).

Occasionally, natural human viral infections induce remissions of leukemia or lymphomas. Inoculation of tumor-bearing patients with live viruses were initiated in the late 1940s. Early studies utilized attenuated liver rabies vaccine to treat melanoma, and induced partial remissions. This was followed by clinical trials to measure the effect of myxo-, paramyxo- and arboviruses on various malignancies. Occasional temporary regressions of tumors were observed, however, regression was eventually followed by regrowth of tumor and death of patients. Other investigators used lymphocytopenic murine virus, live mumps virus or human enteroviruses to treat cancers through various routes including intra-vein, intra-tumor, ingestion, or inhalation, but did not obtained documented cases of cancer cures (Sinkovics and Horvath, 1993).

Parvoviruses are small single-stranded DNA viruses which replicate in the nucleus and are able to infect insects, birds, and a variety of mammals, including humans. The parvoviruses of vertebrates are divided into the groups adeno-associated viruses (AAV) and autonomous parvoviruses on the basis of the requirement of the former for helper viruses such as Ad. The distinction, however, is not absolute. Parvovirus replication depends on host cell factors, some of which are expressed during cell proliferation and differentiation (Cotmore and Tattersall, 1987). The outcome of parvovirus infection is dependent on the physiological state of the host cells. Recent studies have shown that a number of human and murine cells committed to neoplastic transformation are significantly more sensitive to the killing effect of prototype strain MVMp of autonomous parvovirus minute virus of mice (MVM) or H-1 than are their normal progenitors (Cornelis et al, 1988; Cornelis et al, 1990; Spegelaere et al, 1991).

Although the molecular mechanism underlying modulation of autonomous parvovirus-host cell interactions by neoplastic transformation is poorly understood, the potential application of the transformation-dependent replication of the viruses has been considered for development of recombinant vectors for tumor-specific killing (Russell et al, 1992; Dupont et al, 1994). However, preliminary experimental results showed that an additional mechanism is needed for the viral vector to induce effective transformed-cell killing (Personal communication with Dr. Francis Dupont).

Wild-type live human adenoviruses has been utilized to treat cervical cancer (Smith et al, 1956). Large amounts of virus were given to patients through intratumoral, intra-arterial, or intravenous inoculation. An appreciable illness or change other than necrosis of cancer tissue was not observed. The autopsy findings confirmed the clinical observations that the injected virus produced only local effects on the cervical tumor and did not affect the progressive growth of tumor in the pelvic tissues or the development and growth of metastases.

The use of Ad vectors in gene therapy have been rapidly developed. The application potential of the genetically-engineered Ad for gene therapy of cancer has been widely explored with many different strategies (Descamps et al, 1996). Ad vector-mediated delivery of genes encoding such proteins as cytokines, interferons, co-stimulatory molecules or factors have induced anticancer immunity in various animal models (Addison et al., 1995; Zhang et al., 1996). However, the efficacy of this type of approach in treatment of human cancer remains to be determined through clinical trials.

Utilization of Tumor-specific or Tissue-specific Promoter/Enhancer Cassettes

Both immuno-gene therapy and virus-mediated gene therapy for cancer have limitations in either therapeutic efficacy or specificity in cancer cell killing. For the latter, novel approaches have been proposed and tested with the goal of targeting gene expression specifically to tumor cells. Progress has been made in targeting infectious recombinant viral vectors to cells through cellular surface receptors by genetic or biochemical modification of the viral surface. An alternative approach is to target cancer cells at the transcriptional level using lineage-specific promoters that restrict expression of effector genes to tumor cells and related normal cells derived from the same developmental lineage (Hart, 1996). Examples of tumor types that have been targeted in this manner include colon (Osaki et al., 1994; Richards et al., 1995), lung (Osaki et al., 1994; Smith et al., 1994), breast (Manome et al., 1994), hepatocellular carcinomas (Huber et al, 1991; Ido et al, 1995; Kaneko et al, 1995), and melanoma (Vile et al, 1993; Siders et al, 1996).

The application of tumor- or tissue-specific promoter/enhancers has also been used in a therapeutic approach called "virus-directed enzyme/prodrug therapy" (VDEPT) (Huber et al, 1991). These studies demonstrated enhancement of tumor-killing efficacy and reduction of the side effects of such therapy on normal cells (the "bystander effect") by tissue- or tumor-specific driven expression of prodrug-activation genes (Manome et al, 1994; DiMaio et al, 1994).

The α-fetoprotein (AFP) promoter/enhancer cassettes have been utilized to control E1 expression from an Ad vector in order to induce a virus-mediated oncolytic effect on hepatocellular carcinoma (Hallenbeck et al, 1996). As proof of concept for the first generation of a tumor specific replication competent adenoviral (TSRCA) vector, the Ad5 E1 promoter of a wild-type Ad was replaced with a modified version of the AFP promoter. The vectors were shown to replicate in two-thirds of human hepatocellular carcinoma cell lines tested that expressed high levels of AFP. Furthermore, approximately 500–1000 hepatocellular carcinoma cells per virion particle were destroyed in a 13 day assay. Little to no replication was observed in two liver cell lines, two lung cancer cell lines, one colon cancer cell line, and one cervical cancer cell line, each of which do not produce AFP. In addition, investigators tested two primary cultures of normal human lung epithelial and endothelial cells for replication of the vectors since lung tissue is the primary target for Ad replication in human. Neither primary culture supported replication of the vectors, demonstrating the specificity of the vectors in cancer cell killing (Hallenbeck et al, 1996). The investigators also proposed the use of other tumor-specific promoter/enhancers of different cancers using the same type of design as the TSRCA vector.

Therapy of cancer using wild-type viruses seldom results in durable, complete remission. The use of genetically-engineered viral vectors to deliver a gene encoding a toxin, cytokine, or immuno-stimulatory factor has demonstrated certain encouraging results using animal models. However, clinical application of methods is limited by the inability to specifically target the vectors or gene expression to cancer cells. The TSRCA approach has addressed the tumor-specific killing through replication of Ad vectors in cancer cells, which may induce oncolytic effect. This method is limited because tumor regression is limited to the local environment. Additionally, the capacity for insertion of heterologous DNA into the TSRCA vector is limited to less than 4 kb.

The present invention provides a solution to the limitations of current TSRCA methodologies. The reagents and methodologies of the present invention allow for the development of TSRCA vectors carrying multiple gene expression cassettes encoding cytokines, chemokines, tumor suppressors, and/or immunomodulatory factors. The inventions of the present invention will be appreciated by those skilled in the art to address and provide solutions for these significant limitations.

SUMMARY OF THE INVENTION

This invention encompasses a composition for killing target cells, such as tumor cells. The composition comprises a first and a second adenoviral vector that have complementary function and are mutually dependent on each other for replication in a target cell. One of said adenoviral vectors has a target cell-activated promoter or an early gene deletion that controls and limits propagation of the adenoviral vectors in the target cells. One of the adenoviral vectors comprises partial Ad genome which can support the replication cycle of Ad in the target cells. The replication of these vectors in the target cells directly or indirectly kills the target cells. The target cells may be hepatoma, breast cancer, melanoma, lung cancer, colon cancer, or prostate cancer cells, for example. The vectors of this invention may also be utilized to treat other diseases such as restenosis, in which case the target cell may be a vascular smooth muscle cell.

The present invention also comprises an adenoviral vector (the "controlled vector") that comprises a promoter that is activated in a tumor cell and is operably linked to the Ad E1 gene. The products of the E1 gene control the replication of the Ad vector in tumor cells. A deletion of the AD E1 gene can also be used to render the controlled-Ad a capability to specifically drive the viral replication in the tumor cells. The controlled vector may also contain a cassette to express an immunomodulatory protein such that the protein is expressed in the tumor cell. The tumor-activated promoter may, for example, be the α-fetoprotein promoter, the DF-3 mucin enhancer, the tyrosinase promoter, the carcinoembryonic (CEA) promoter, the prostate specific antigen (PSA) promoter, or the $H_1$ parvovirus promoter. The immunomodulatory protein may, for example, be an interferon (IFN) such as IFN-γ, a B7 co-stimulatory molecule such as B7.1, an interleukin, a chemokine or a tumor-specific antigen. For other applications, the promoter also can be cell cycle specifically inducible or synthetic promoters/enhancers.

This invention also comprises a "supplemental vector" which provides proteins required for replication of the controlled vector and the supplemental vector in the tumor cell.

This invention also includes methods of making and purifying the vectors of the invention by transfecting cell lines in which the vectors can replicate and are packaged in large amounts. Purification may be completed using a biochemical technique such as cesium chloride (CsCl) centrifugation, for example.

The present invention further provides a modified adenoviral vector which: 1.) increases the capacity of the vector for carrying one or multiple therapeutic genes; 2.) targets adenoviral replication to a specific type of host cell or tissue by providing genes (with or without deletion) encoding the AdE1 proteins operably linked to a cell type or tissue-specific transcriptional regulatory region; 3.) induces expression of an immunomodulatory protein or proteins within a tumor cell to increase the immune response against local and distant sites of tumor growth; 4.) provides a composition of tissue specific mutually dependent adenoviral vector hereinafter referred to as "complementary-Ad vector system" that induces expression of an immunomodulatory protein and transcriptionally targets adenoviral replication to specific cell types.

It is an objective of the present invention to provide vectors and methodologies needed to combine the specific tumoricidal effect of Ad vectors with induction of systemic anticancer immune responses by delivery of effector genes such as cytokines, chemokines, tumor antigens, MHC molecules, cell adhesion molecules, and/or other immuno-modulating factors. Preferably, the present invention provides a controlled-Ad vector having large gene-carrying capacity that may be utilized to deliver single or multiple expression cassettes comprising immunomodulatory or tumor suppressor genes. Ideally, the complementary-Ad vector system induces a local specific-tumoricidal effect together with a systemic anticancer immune response. Therefore, it is further an objective of the present invention to provide specific tumor cell killing at local and remote sites for elimination of primary and metastatic cancer cells.

It is yet another objective of the present invention to provide two Ad vectors that complement each other for replication and have separate roles in lysing tumor cells and delivering effector genes. The present invention therefore provides a supplemental-Ad vector, having an E1 region deletion or substitution and a modified or unmodified packaging signal, and that provides the viral DNA replication and capsid proteins necessary for packaging of the controlled-Ad. In a preferred embodiment the supplemental Ad vector has a modified packaging signal and the controlled-Ad vector has a wild-type packaging signal to gain packaging advantages over the supplemental Ad vector and the E1 region controlled by a tissue-specific or tumor-activated promoter/enhancer cassette for trans-activation of the supplemental-Ad transcription and replication.

It is also an objective of the present invention to provide tumor-directed cytokine gene transfer such that the cytokine is produced locally, thus providing an immunologically more efficient system and does not cause systemic toxicity. The combination of significant undesired effects and marginal therapeutic outcomes from systemic administration has stimulated efforts to genetically engineer tumor cells to produce the cytokines themselves (Rosenberg et al, 1989).

It will be understood by those skilled in the art that the present invention is not limited in application to gene therapy of cancer. Other applications of the present invention are contemplated.

The length Ad5 genome is about 36 kb, divided into 100 map units (mu). The dotted arrows represent early (E) transcription and the solid arrows represent late (L) transcription. The directions of transcription are indicated by arrows. Gaps between arrows indicate intervening sequences. The box represents location of the major later promoter and tripartite leader sequences (MLP). The solid triangle at 1 mu represents the location of the packaging signal.

Figure 1:
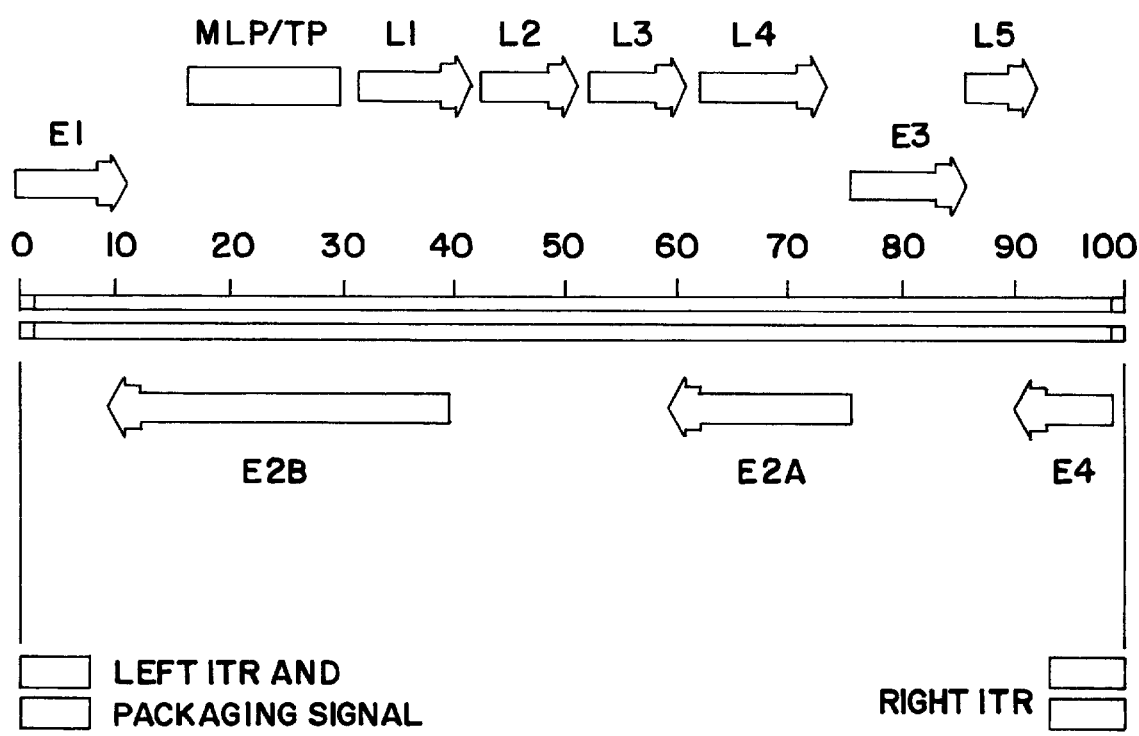
FIG. 1. The genome and transcription units of Ad5.
Figure 2:
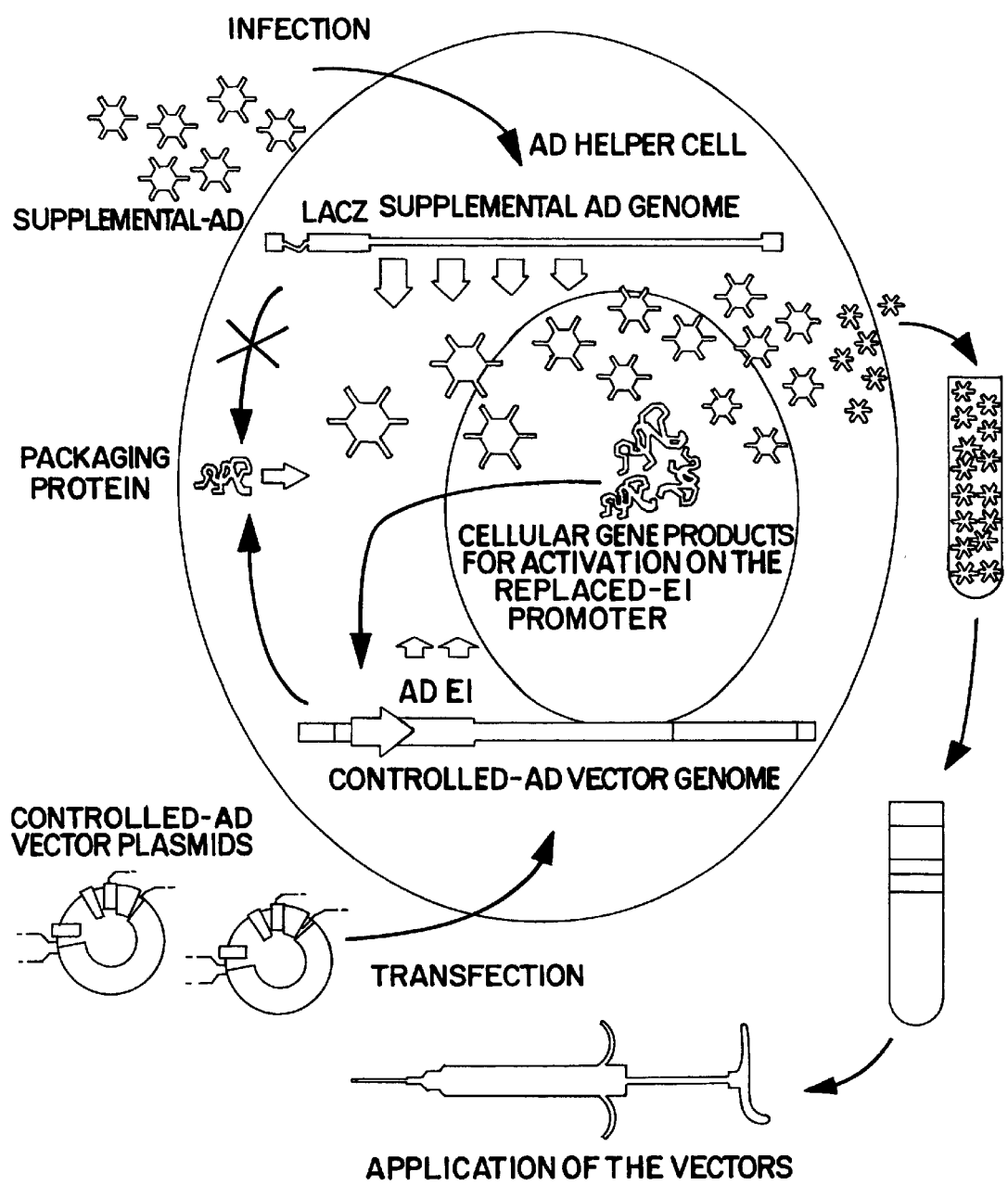

FIG. 2. The principle of the complementary-Ad vector system.

Shown are two major components of the system: the supplemental-Ad, and the controlled-Ad vector. With the E1-transactivation from the helper cell by activation of the specific promoter/enhancer carried by the controlled-Ad, the supplemental-Ad replicates itself and produces the late proteins to form capsids. However, the packaging of the supplemental-Ad genome into the capsid is inefficient due to the packaging attenuation associated with the supplemental-Ad. In the presence of the controlled-Ad vector genome, the supplemental-Ad also supports the DNA replication of the controlled-Ad vector genome, which is preferentially packaged due to its wild-type packaging signal that has high affinity to the limiting amount of the packaging proteins. Further purification of the Ad vectors can be achieved by biochemical or physical method, such as ultracentrifugation.

FIG. 3 (parts A–C). The packaging signal of Ad5.

Shown is the sequence and position of the packaging signal of Ad5 at the left end of the viral genome. There are 7 A-repeats identified as the packaging signal motifs. The consensus sequence of the A-repeat is proposed at the bottom of the figure.

FIG. 4 (parts A–B). The prototype of the supplemental-Ad and the controlled-Ad vectors.

Shown is the general structure of the helper virus and the controlled-Ad vectors. The latter have up to 36-kb gene delivery capacity that can be quipped with single or multiple gene expression cassettes.

FIG. 5 (parts A–C). Basic composition of the oncolytic/immunogenic Ad vector system.

The basic elements of the system are the supplemental-Ad vector and the controlled-Ad vector. (A) The supplemental-Ad is similar to the E1-substituted first generation Ad, but has a partial deletion of its packaging signal. The E1 region is replaced by a reporter gene, here is the lacZ gene for $\mu$-gal protein. (B) The controlled-Ad, containing only the minimal cis-element of Ad genome (two ITRs with the packaging signal), carries a promoter/enhancer to drive the Ad E1 gene (Ad5E1). The promoter/enhancer is activated specifically in target cell, such as a cancerous or transformed cell. The AdE1 gene under the control of this element is specifically transcribed in tumor cells. The E1 protein then trans-activates the genome of the supplemental virus that has the E1 region substituted by a reporter gene and also has a manipulated packaging signal such that packaging of the controlled-Ad is preferred in the cell. The supplemental virus, activated by the E1 proteins, is able to replicate in the tumor cells, resulting in lysis of those cells.

Figure 6:
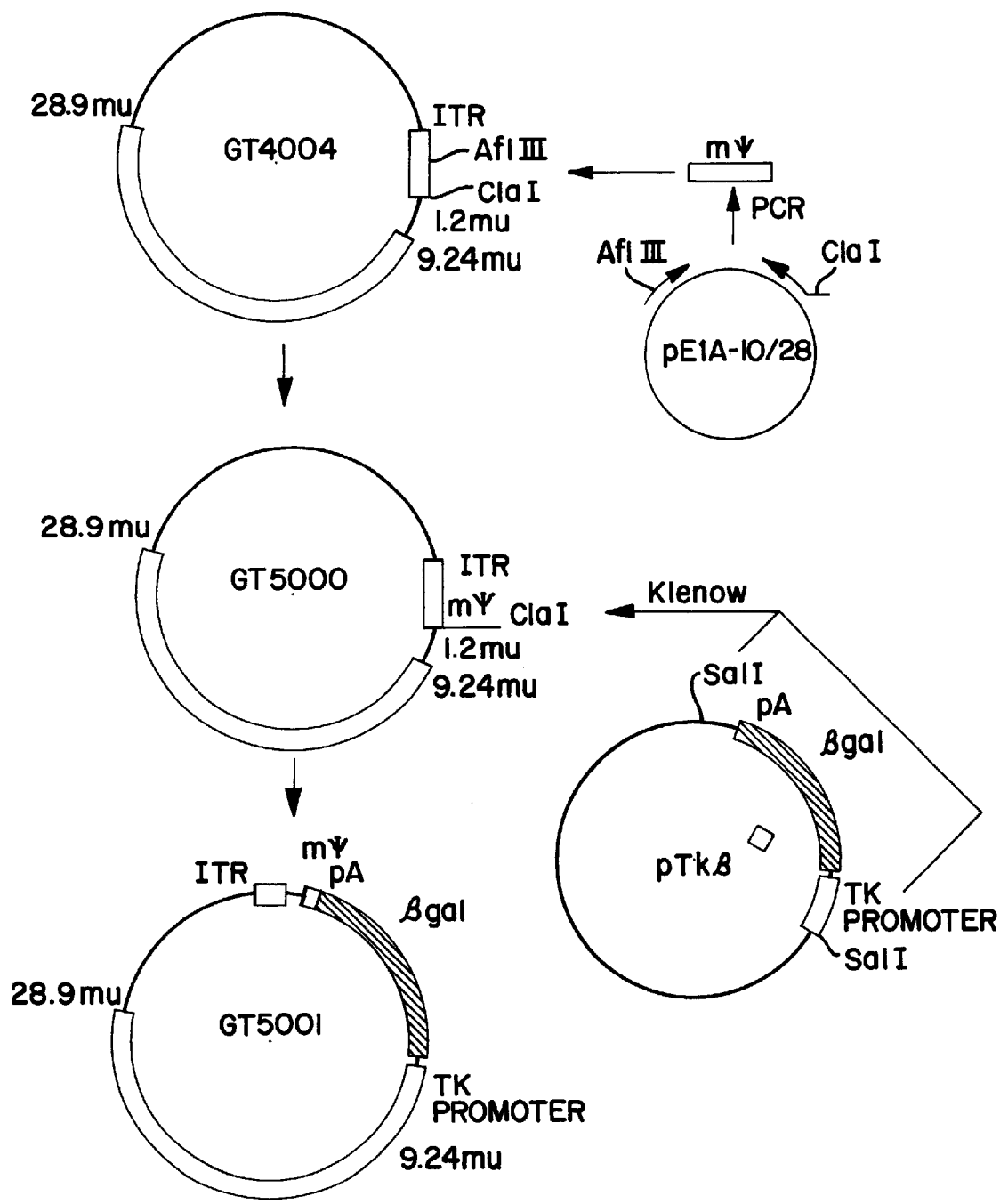

FIG. 6. Construction of the shuttle vector to generate the packaging attenuated supplemental-AdHβ.

To construct GT5000, the mutant packaging signal sequence, mt Ψ, was amplified by PCR and substituted in a shuttle vector with an Ad5 sequence extended until 28.9 mu (GT4004). A β-gal expression cassette from pTk-β was cloned into the E1-deletion of GT5000 to give the final shuttle vector GT5001.

Figure 7A:
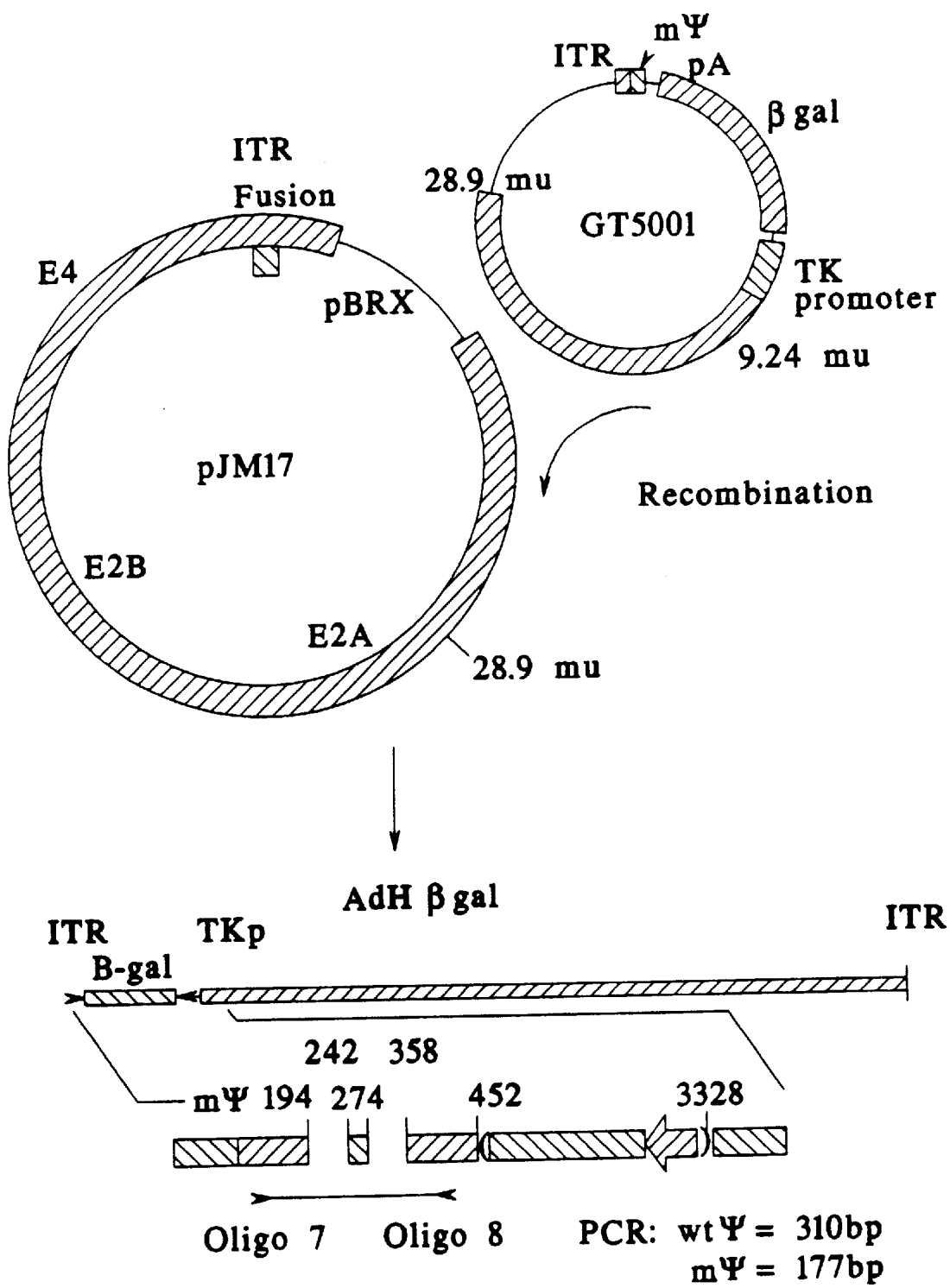
Figure 7B:
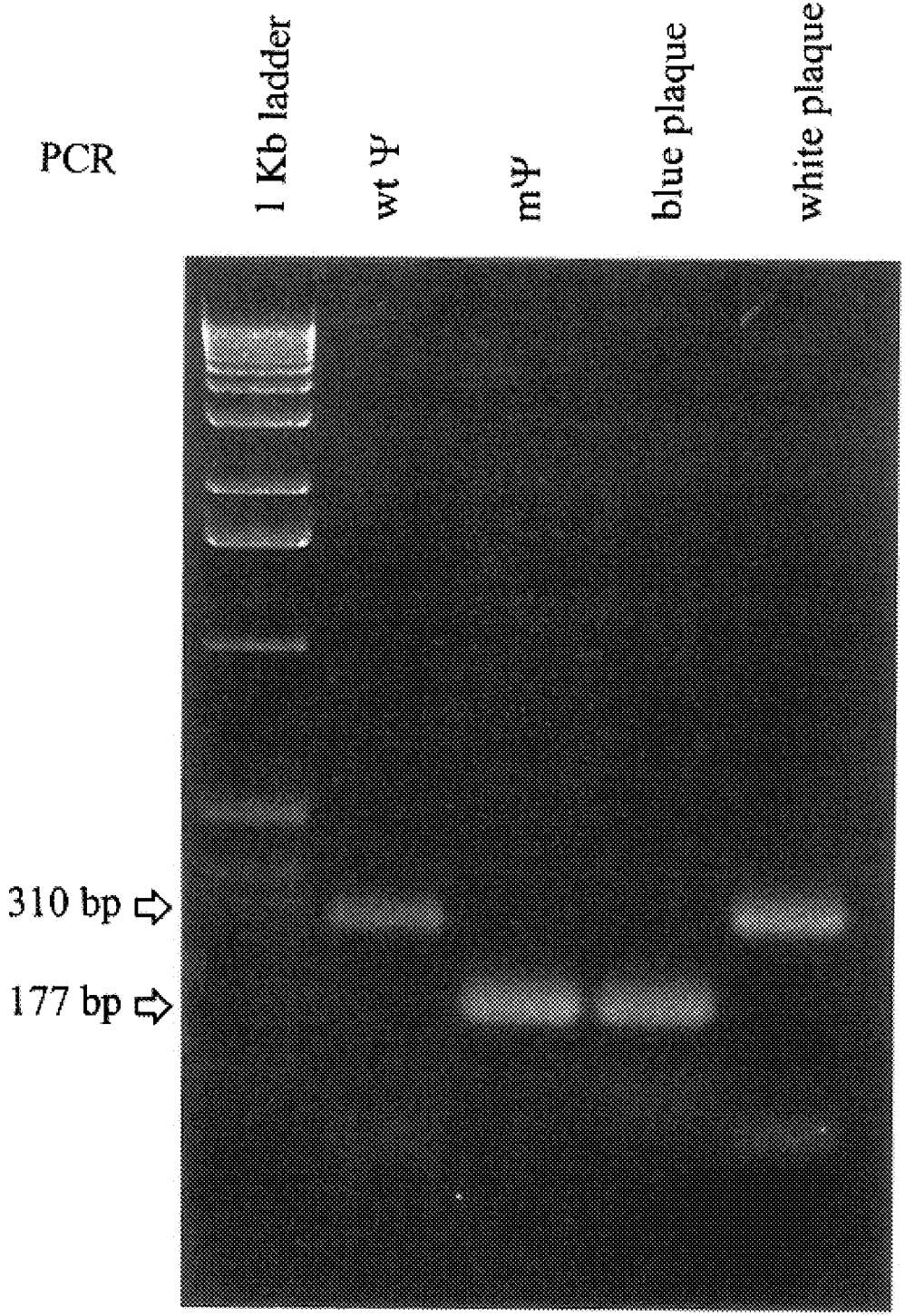

FIG. 7. Generation of AdHβ.

The shuttle vector GT5001 (see FIG. 6) was cotransfected with pJM17 in 293 cells. Recombination in the homologous 7 Kb region between these plasmids (9.24 to 28.9 mu of Ad5) yields a packageable virus with the left part coming from GT5001. The numbers in the left region of AdHβ shown at the bottom correspond to Ad5 nt sequence and indicate the extension of the double deletion in the packaging signal and the deletion in E1 where the β-gal expression cassette is inserted. After two weeks of this cotransfection, several blue plaques were isolated and the mutation in the packaging signal was analyzed by PCR with oligos 7 an 8. The size of the amplified fragment, 310 bp for the wild type packaging signal (wt Ψ) and 177 bp for the mutant packaging signal (mt Ψ), can be distinguished in a 2% agarose gel as shown. 1 Kb ladder, 1 Kb DNA ladder marker from Gibco BRL (Gaithersburg, Md.); wt Ψ and mt Ψ PCR controls where vDNA was extracted from an E1-deleted vector, Ad-CMVβgal, and from dl10/28 virus respectively;

blue plaque, vDNA from a plaque that stained blue with X-gal; white plaque, vDNA from a plaque that did not stained blue with X-gal.

Figure 8:
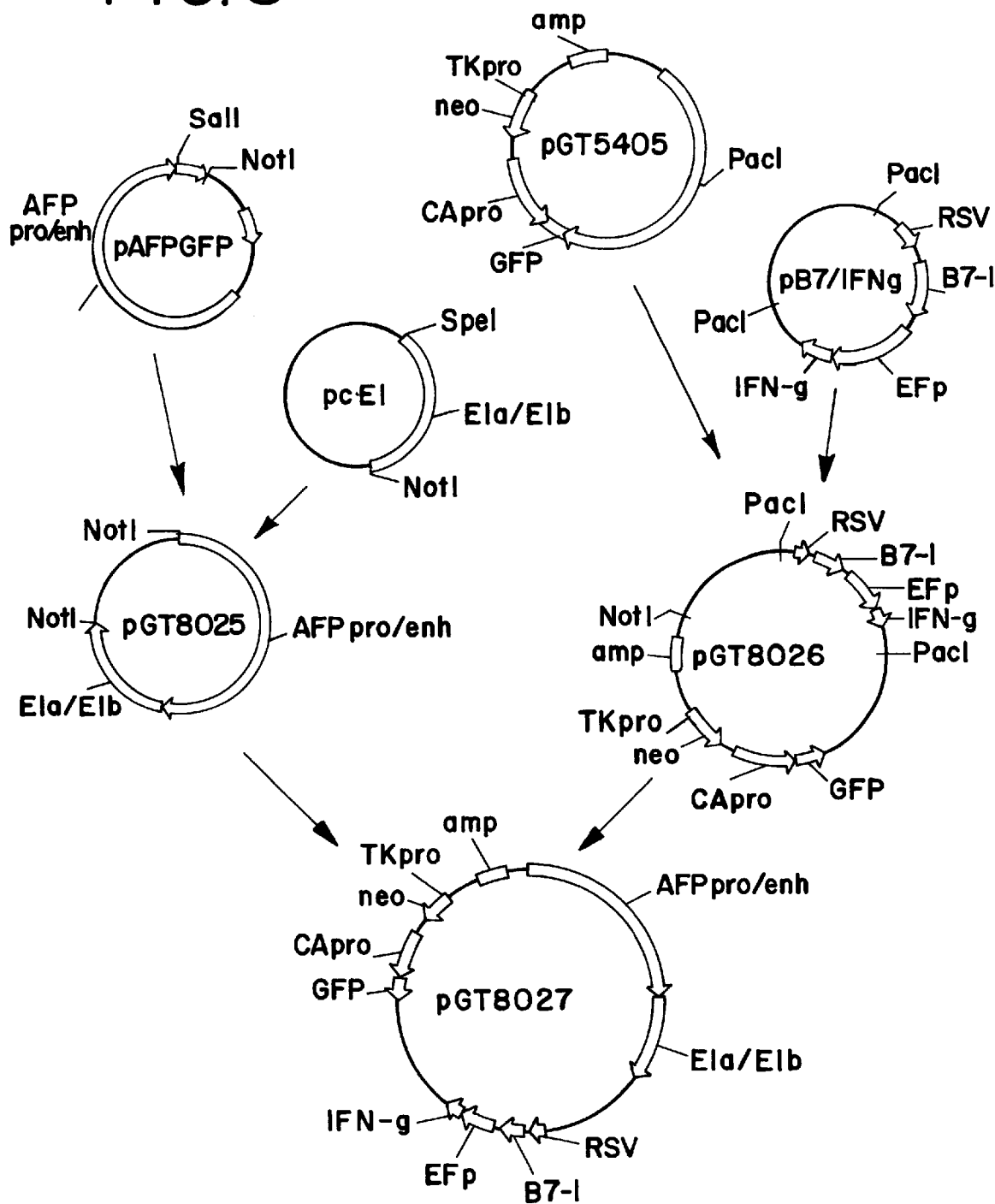

FIG. 8. Cloning of controlled-Ad vector pGT8027

A fragment containing the E1 genes was inserted downstream of AFP promoter in pAFPGFP to form pGT8025. Expression cassettes of RSV/B7 and EFp/IFN-γ were cloned into Ad vector pGT5405 at Pac I site forming pGT8026. The E1 genes under control of AFP promoter were then inserted into pGT8026 at Not I site to generate the final controlled vector pGT8027.

Figure 9:
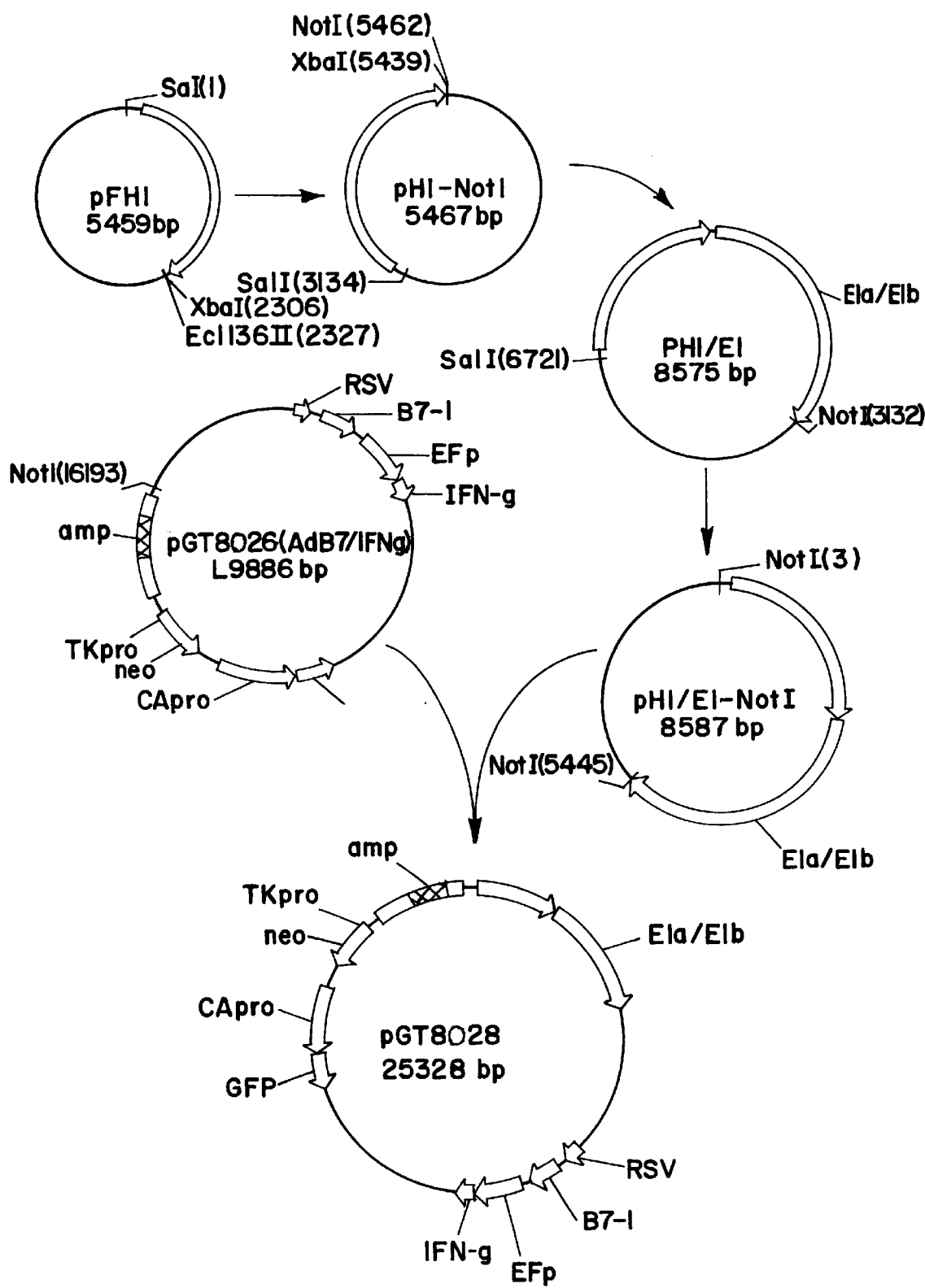

FIG. 9. Cloning of controlled-Ad vector pGT8028

A fragment containing the E1 genes was inserted downstream of partial genome of H1 autonomous parvovirus which contain the p4 and p38 promoters and the complete NS1 gene. The E1 genes under control of the p4 and p38 parvovirus promoter were then inserted into pGT8026 at Not I site to generate the final controlled vector pGT8028.

FIG. 10 (parts A–C). Variation possibilities of the oncolytic/immunogenic complementary-Ad vectors Shown are the variable structures of the supplemental-Ad (A) and controlled-Ad (B) that can be designed in accordance with the need of application. The critical aspect of the variation is that the two vectors complement each other in Ad genome function such as E1 genes and/or other early genes. The complementation elements of the two vectors are listed in the Table (C). The transgene and supporting elements were mainly included in the controlled-Ad vectors, but this does not exclude the requirement for the supplemental-Ad for those elements in certain circumstances. Deletion of an early Ad gene that encodes the cell cycling inducer will abrogate the replicative capability of adenovirus in the normal resting cells, but allow the controlled-Ad specifically drive replication and propagation of the complementary-Ad vectors in tumor cells that have defect in the counterpart of the deleted viral gene product. Two examples are the viral proteins E1b-p55 and E1a that are dispensible for virus propagation in p53-deleted (or mutated) or retinoblastoma-deleted (or mutated) tumor cells, respectively.

Figure 11:
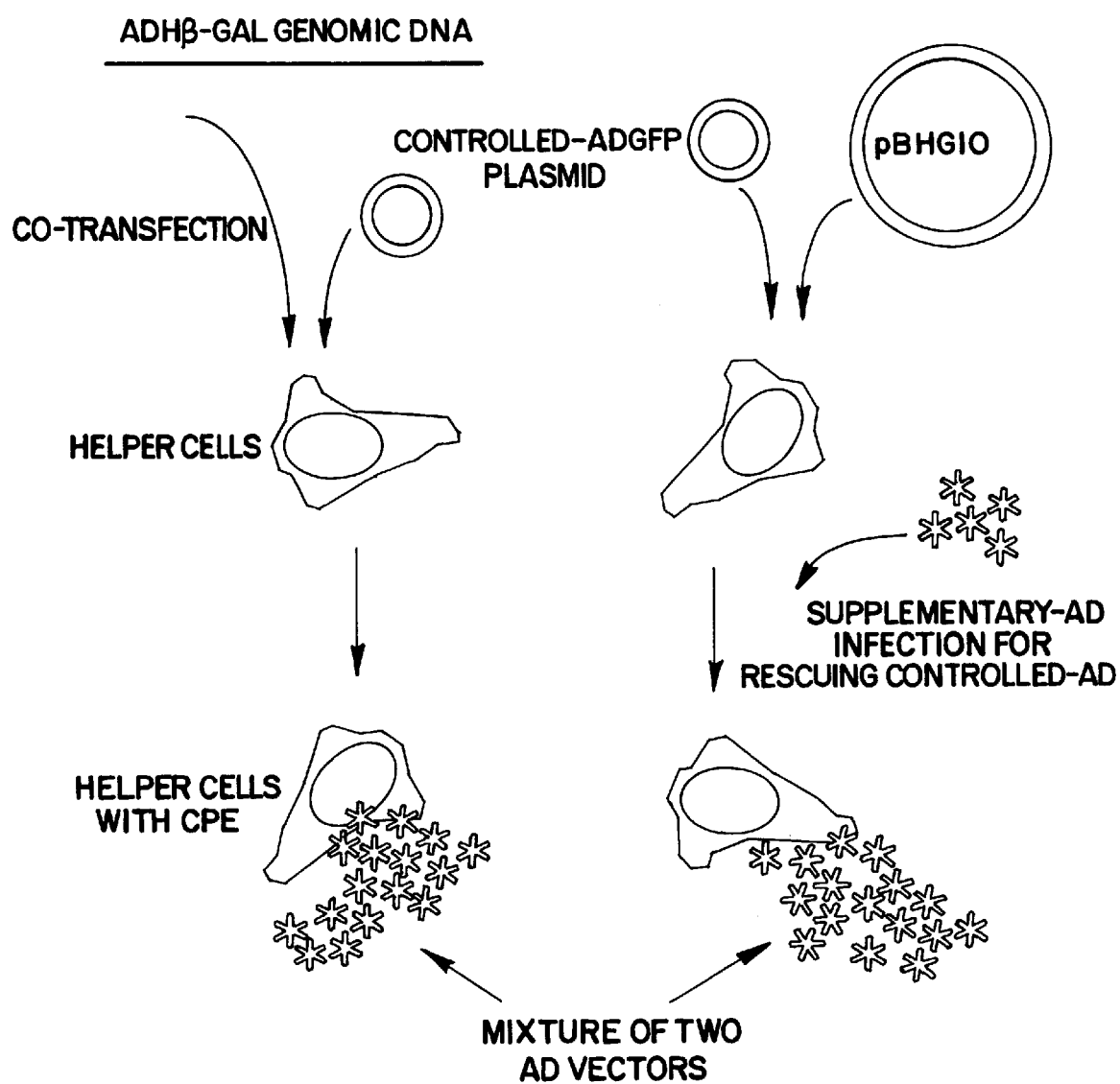

FIG. 11. Methods for generation of the complementary-Ad vector system.

To generate the complementary-viral vector system, two different complementation protocols can be used that may give similar yields. In the first one the controlled-Ad plasmid is co-transfected with vDNA from AdHβ, and the helper cells are cultured until CPE is observed. In the second method, three days after an initial co-transfection of the controlled vector plasmid with pBHG10, AdHβ is added as supplemental virus, and the cells are cultured until CPE is observed.

Figure 12:
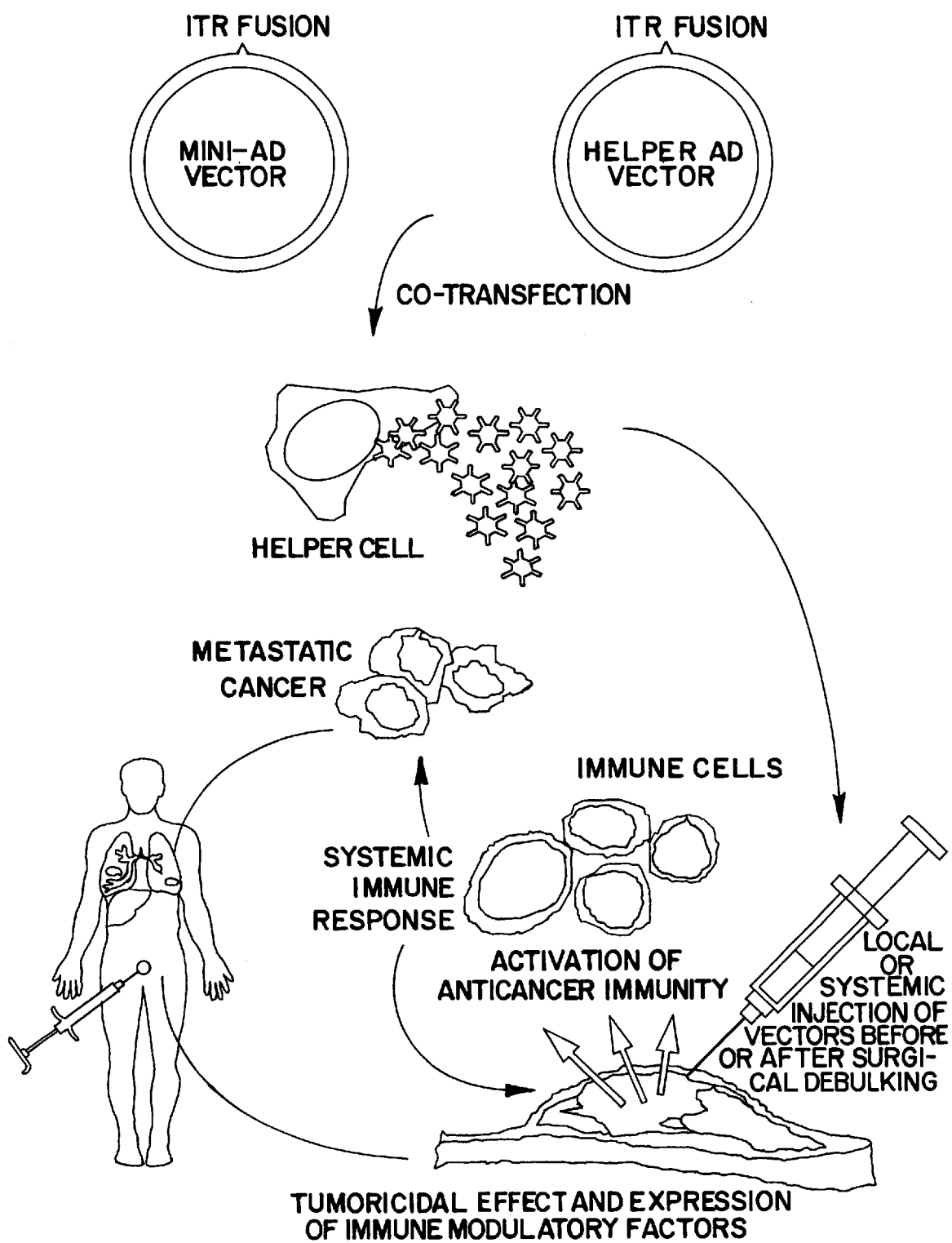

FIG. 12. Clinical application approach of the oncolytic/immunogenic complementary-Ad vector system.

Oncolytic controlled-Ad are generated by co-transfection of two plasmids in a helper cell line: The controlled-Ad plasmid contain one or more Ad genes regulated by a tumor-activated promoter/enhancer, the supplemental-Ad plasmid contains the remainder of the Ad genes, and the helper cell line is a tumor-derived cell line in which the tumor-activated promoter of the controlled-Ad is functional. The controlled-Ad and the supplemental-Ad complement each other in the supplemental cell line and propagate as a virus mixture. The vector mixture can be purified through CsCl gradients and injected locally or systemically the tumor mass or the tumor bed following surgical debulking.

The tumor-activated promoter/enhancer specifically transcribes in tumor cells the AdE1genes to produce E1A and E1B proteins that transactivate transcription and replication of the supplemental-Ad. The controlled-Ad vector also replicates with the propagation of the supplemental-Ad. The replication of the controlled-Ad produces high copy numbers of the controlled-Ad genome, which supports high level expression of the immunomodulatory genes to induce specific anti-cancer immunity. Propagation of the supplemental-Ad in the tumor cells results in lysis of the tumor cells. This system generates a local tumoricidal effect and a systemic antitumoral response that results in rejection of distant metastases.

DETAILED DESCRIPTION OF THE INVENTION

It will be appreciated by those skilled in the art that the present invention provides reagents and methodologies that substantially improve current gene therapeutic technologies used for the treatment of cancer and other diseases. The present invention provides mutually-dependent complementary tissue specific replicable adenoviral (Ad) vector system useful for the treatment of neoplasia and other diseases. The system may comprise a controlled-Ad vector, a supplemental-Ad. The controlled-Ad has minimal Ad cis-elements (inverted terminal repeats or "ITR" and a packaging signal) and a tumor- or tissue-specific promoter/enhancer cassette driving expression of the Ad E1 genes. The controlled-Ad may have an AdE1 deletion. The controlled-Ad vector further comprises an expression cassette having a gene of interest such as an immunomodulatory gene or other Ad early-region gene. The supplemental-Ad comprises an attenuated packaging signal, a deletion of the E1 region, and the remainder of the Ad genome with or without substitution. The Ad vectors thus produced using this system comprise a pair of human recombinant adenoviruses that are mutually dependent, and are termed "complementary Ad vectors". The most direct application of the system is gene therapy of cancer. Upon local or systemic injection to infect a tumor mass, the vectors can preferentially replicate in tumor cells and express immunomodulatory proteins, which preferably results in a local tumoricidal effect and induction of a systemic anticancer immune responses.

Those skilled in the gene therapy arts will recognize techniques useful in practicing the present invention. *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), PCR *Protocols: A Guide to Methods and Applications* (Innis, et al. 1990. Academic Press, San Diego, Calif.), *Culture of Animal Cells: A Manual of Basic Technique, 2$^{nd}$* Ed. (R. I. Freshney. 1987. Liss, Inc. New York, N.Y.), *Antibodies: A Laboratory Manual* (Harlow and Lane. 1988. Cold Spring Harbor Laboratory, Cold Spring Harbor, N.Y.), Guide to Protein Purification: Methods in Enzymology, Vol. 182 (M. P. Deutscher, ed. Academic Press, San Diego, Calif.).

Within this application, DNA molecule is defined a plasmid, virus, autonomously replicating sequence, phage or linear segment of a single- or double-stranded DNA or RNA derived from any source.

A reporter construct is defined as a subchromosomal and purified DNA molecule comprising a gene encoding an assayable product.

A gene expressed in a tissue-specific or tumor-specific manner is that which demonstrates a greater amount of expression in one tissue as opposed to one or more second tissues in an organism.

An effector gene is defined as any gene that, upon expression of the polypeptide encoded by the gene, confers an effect on an organism, tissue or cell.

Heterologous DNA is defined as DNA introduced into an adenoviral construct that was isolated from a source other than an adenoviral genome.

A transgene is defined as a gene that has been inserted into the genome of an organism other than that normally present in the genome of the organism.

A recombinant adenoviral vector is defined as a adenovirus having at least one segment of heterologous DNA included in its genome.

Adenoviral particle is defined as an infectious adenovirus, including both wild type or recombinant. The adenovirus includes but is not limited to a DNA molecule encapsidated by a protein coat encoded within an adenoviral genome.

A recombinant adenoviral particle is defined as an infectious adenovirus having at least one portion of its genome derived from at least one other source, including both adenoviral genetic material as well as genetic material other than adenoviral genetic material.

A treatable condition is defined as a condition of an organism that may be altered by administration of a form of treatment including but not limited to those treatments commonly defined as being of medicinal origin.

An antigen is defined as a molecule to which an antibody binds and may further include any molecule capable of stimulating an immune response, including both activation and repression or suppression of an immune response.

A tumor suppressor gene is defined as a gene that, upon expression of its protein product, serves to suppress the development of a tumor including but not limited to growth suppression or induction of cell death.

A growth suppressor gene is defined as a gene that, upon expression of its protein product, serves to suppress the growth of a cell.

An oncogene is defined as a cancer-causing gene.

An immunomodulatory a gene is defined as any gene that, upon expression of its nucleic acid or protein product, serves to alter an immune reaction.

A genetic condition is defined in this application as a condition of an organism that is a at least partially the result of expression of at least one specific gene including but not limited to the wild-type form of that gene and any mutant form of that gene.

An expression cassette is a DNA fragment comprising a coding sequence for a reporter or effector gene operably linked to a transcriptional regulatory region or a transcriptional control region sufficient for expression of the encoded protein in an appropriate cell type.

Most adenoviral vectors currently in use by those skilled in the art are deleted in the E1 region and propagated in a 293 cell line that provides the missing E1 functions (Graham et al, 1977). In other cases, helper viruses have been used to package vectors containing large deletions of the viral genome. However, a major disadvantage of such systems is that the majority of the virus packaged is helper virus (similar to, in the present invention, the supplemental-Ad). The applicants have previously demonstrated in U.S. patent application Ser. No. 08/658,961 filed May 31, 1996 complementation of large deletions in the Ad vector genome by a helper vector having a partial deletion of the packaging signal. The application is incorporated herein by reference. The supplemental vector also has the E1 region substituted by a β-gal expression cassette and needs, therefore, to be propagated in 293 cells. The supplemental vector complements the controlled-Ad vectors having those the adenoviral genes deleted.

In the present invention, the term "controlled-Ad vector" refers to a vector in which, with the exception of the E1 gene region, adenoviral coding sequences are deleted and the vector comprises the minimal elements necessary for replication and packaging. The "supplemental-Ad vector" provides proteins required to maintain replication and packaging of both the controlled-Ad vector and the supplemental-Ad vector. In the present invention, a controlled-Ad vector comprising the early Ad gene or genes (E1, E4 or E2) that are missing in the supplemental-Ad vector is provided. With this additional sequence, the controlled-Ad may support replication of the supplemental-Ad (acting as a helper of the helper). Therefore, the two vectors, the supplemental-Ad and the controlled-Ad, are mutually dependent upon one another for propagation.

To confer tumor-specific propagation of both the supplemental-Ad and the controlled-Ad, the promoter of one or more of the early genes necessary for adenoviral replication is substituted by a tumor-specific, tumor-activated or inducible promoter. Any adenoviral gene necessary for replication may be utilized, such as E1, E2, and E4; and any promoter showing tumor-specific activity may be used, such as α-fetoprotein, CEA, melanotransferrin, Erb-B2, tyrosinase, MUC1, PSA, for example. Specifically, the present invention comprises a controlled-Ad vector containing the E1 region with the E1A promoter substituted by the α-fetoprotein promoter. Only cells that are able to utilize the α-fetoprotein (AFP) promoter and that have been co-infected with the controlled-Ad and the supplemental-Ad (i.e., at the site of injection) supports propagation of the controlled-Ad and the supplemental-Ad. As both viruses are produced in similar amounts (due to the effect of the partial deletion or modification in the packaging signal of the supplemental-Ad), neighboring cells will be co-infected and, if those cells are able drive E1 expression from the AFP promoter (as many hepatocellular carcinoma tumor cells do), both viruses will continue to propagate. The farther the distance from the injection site (tumor or tumor bed after surgery), the lower the chances of co-infection and therefore vector spread is halted. This may be an important safety advantage over a single oncolytic vector scenario where, with a leaking tumor-specific promoter, the vector spread could be systemic. Another advantage of this invention over the prior art is that the combination of two defective vectors allows much more room for therapeutic heterologous DNA. In a single oncolytic Ad vector carrying a tumor-specific promoter to substitute the Ad E1 promoter, there is less than 4-kb room for additional effector genes into the vector. In the present invention, the capacity of the controlled-Ad for exogenous non-viral DNA is up to 36 Kb. Any gene with an antitumor potential can be incorporated into the controlled-Ad. In one preferred embodiment, immuno-stimulatory genes such as the co-stimulatory molecule B7.1 and the interleukin IFN-γ are incorporated into the controlled-Ad as two expression cassettes.

1. The Complementary-Ad Vector System a. Composition of the system: The complementary-Ad vector system consists of two major parts: (1) a packaging-attenuated supplemental-Ad vector which is E1 deleted or substituted and (2) the cognate Ad vector that only have a minimal amount of cis-element of the viral genome have E1 or other early stage genes, referred to as the controlled-Ad vector. These vectors can be propagated in Ad helper cell lines that allows E1 trans-activation like 293 cells and/or regulation of packaging signal for the supplemental-Ad. The supplemental-Ad has all of the viral genes and elements that can be used for replicating itself and trans-complementing the controlled-Ad vectors, except that it has an E1 deletion or substitution and a manipulated packaging signal that can be used to control or discriminate itself in the process of packaging the controlled-Ad vectors. The controlled-Ad vectors, on the other hand, has the ITRs and wild-type packaging signal that are cis-elements for Ad DNA replication and packaging. The controlled-Ad can be controlled by two different ways: promoter replacement and/or functional deletion:

(1) Promoter replacement: The natural viral promoter of the early gene for control of viral replication can be substituted by a heterologous promoter, which is active or inducible only in the target cells. For example, the E1 a promoter of adenovirus is the initiator of the viral replication cycle. The E1a promoter can be replaced by the α-fetoprotein promoter, which is active mainly in hepatocarcinoma cells. Other examples of promoters that are lineage-specific or can be specifically activated in tumor cells are listed in FIG. 5C.

(2) Functional deletion: An adenoviral gene that is not essential for the viral replicative cycle in the target cells can be deleted, which can differentiate the viral specific propagation in the target cells from that of non-permissive in non-target cells. For example, tumor cells are usually the cells in cycling so the adenoviral functions to induce cycling of normal resting of cells are no longer needed. Deletion of the adenoviral gene encoding the cell cycling inducer will abrogate the replicative capability of adenovirus in the normal resting cells. Two examples are the viral proteins E1b-p55 and E1a that are dispensible for virus propagation in p53-deleted (or mutated) and retinoblastoma-deleted (or mutated) tumor cells, respectively. The rest of the controlled-Ad vectors consists of transgene or heterologous DNA. Ad helper cell lines similar to 293 cells have the capacity to activate the promoter driving the Ad E1 genes for trans-activating the supplemental-Ad transcription and replication. The cells may also have control mechanisms for the packaging attenuation of the supplemental-Ad. These cells may be used to propagate the supplemental-Ad without the aid of the controlled-Ad.

b. Mechanism of operation of the system: The design of this system is to have the tissue-specific or tumor-activated promoter activated in the helper cells or target tumor cells. The promoter drives the transcription of the E1 gene carried by the controlled-Ad. The E1 gene products can in turn drive the transcription and replication of the supplemental-Ad genome. The controlled-Ad genome can also be replicated simultaneously. Because the packaging protein of Ad is a trans-acting factor present in low amount in the infected cells and is the rate-limiting step for the packaging of Ad. As the wild-type packaging signal is recognized by the packaging protein with higher affinity than the engineered signal, packaging of the supplemental viral genomes with the mutations in packaging signal can be partially or completely suppressed in the presence of the controlled viral genomes with wild-type packaging signal, which ensures a preferential packaging of the controlled-Ad vectors. Thus, the two viral vectors are mutually dependent. Further deletion or substitution of the supplemental-Ad in the other early regions (E2, E3, and/or E4) and equipment of the controlled-Ad with the corresponding genes may increase the packaging and titer of the controlled-Ad and more dependence of the supplemental-Ad on the controlled-Ad. This is particularly useful for development of anticancer complementary-Ad vectors. The complementary-Ad vectors may be further purified through biological, biochemical, or physical methods such as ultracentrifugation through CsCl gradient, if purification of the Ad vectors is required for application (FIG. 2).

c. Capability of the system: High gene-delivery capacity is one of the major features of this complementary-Ad vector system. Both Ad vectors can carry heterologous DNA. The maximal packaging capacity is about 105% of the genome, i.e. about 38 kb (Ghosh-Choudhury et al, 1987). Since the size of the viral cis-element in the controlled-Ad vector can be trimmed to less than 1 kb, and the deletion E1 and E3 gene in the supplemental AD can add another 8 kb room, the total capacity of the complementary-Ad vectors to carry heterologous DNA can theoretically be up to 45 kb. The heterologous DNA can be either transgene expression cassettes or regulatory elements. The expression cassettes can be single or multiple, bicistronic or polycistronic. The regulatory elements can be DNA sequences for controlling transgene retention, transcription, and vector targeting. All of these become possible due to the room created in the complementary-Ad vectors.

2. The Packaging-Attenuated Supplemental-Ad a. The prototype structure of the supplemental-Ad: The supplemental-Ad vectors have two structural features: containing partial wild-type Ad genome and engineered packaging signal (FIG. 3). To depend on the controlled-Ad vector, the supplemental-Ad must be defective in replication, such as the current E1-deleted or substituted. For the purpose of control of its packaging in the presence of the controlled-Ad vector, the supplemental must be also attenuated in packaging (detailed in below). Therefore, the general structure of the supplemental-Ad can be summarized as an Ad vector that has all of the wild-type genome except that the E1 region and packaging signal are manipulated. However, the other essential regulatory genes of Ad such as E2 and E4 can also be manipulated or substituted. The viral genome can also be split into different pieces in order to further disable the replication competence of the supplemental-Ad or to reduce the genome size of the supplemental-Ad for facilitating the replication and packaging of the controlled-Ad vectors. As long as the titer of the supplemental-Ad will not be significantly affected, both defect in viral replication and attenuation in packaging of the supplemental-Ad should be considered in the design of the structure of the supplemental-Ad.

b. The general function of the supplemental-Ad: The primary function of the supplemental-Ad is to supply capsids for packaging of the controlled-Ad vectors and lyse the target cells through viral propagation. In order to fulfill this function, the supplemental-Ad must be able to reproduce itself, although it is dependent on the activation of the tissue-specific promoter by the target cells on the E1 genes that are carried by the controlled-Ad. The DNA replication and transcription of the supplemental genome is not affected. Otherwise, the yield of the late gene products (the capsid proteins) will be affected accordingly and the titer of the controlled-Ad vectors will be reduced. The stringency of packaging attenuation of the supplemental-Ad can be greatly reduced. The supplemental-Ad under this condition may also function to deliver transgenes together with the controlled-Ad vectors.

c. The designs for packaging attenuation: The purpose for attenuation of packaging the supplemental-Ad is to reduce the potential for the supplemental-Ad over grow on the controlled-Ad vectors. This is especially important when relatively high titer of the controlled-Ad vectors was required for a particular application. The packaging function of the supplemental-Ad is designed to be defective not completely but disabled, because the supplemental-Ad must remain together with the controlled-Ad vector forming a complementary-Ad vector system. The followings are the possibilities of designs for packaging attenuation of the supplemental-Ad.

Packaging signal mutation: The Ad5 packaging signal is composed of a repeated element that is functionally redundant (Hearing et al, 1987) (FIG. 4). Partial deletions of the packaging signal elements have been shown to reduce the yield of mutant Ad from several fold to approximately a hundred fold that of the Ad with wild-type packaging signal (Grable and Hearing, 1992). The design of the packaging signal mutation therefore incorporates a partial deletion of the motifs of the A-repeats from the wild-type Ad packaging signal.

Synthetic packaging signal: Since the Ad5 packaging signal has a consensus A (adenosine) enriched motif (e.g. A-repeat: TAAATTTG), incorporation of an array of tandem repeats of a selected A-repeat or any synthetic DNA motifs may change the affinity of the artificial packaging signal to the packaging proteins and alternate packaging of the supplemental-Ad.

Packaging signal interference: The Ad packaging signal is actually a specific DNA sequence that can be recognized and bound by the packaging proteins. In order to interfere with the effective binding of the packaging proteins to the signal, other DNA binding sequences can be put within or adjacent to the A-repeat array of the packaging signal of the supplemental-Ad. The inserted binding sites will allow a high-affinity binding by their cognate DNA binding proteins that can positionally compete off the binding of the Ad packaging proteins to the Ad packaging signal, especially under the condition that the packaging signal of the supplemental-Ad has been mutated and the affinity of binding by the packaging proteins has been reduced.

Packaging signal relocation: The Ad packaging signal is naturally located at the left end of the wild-type Ad genome. There are reports that the packaging signal can be put at the right end and still be functional. This evidence indicates that the packaging signal is relocatable. A design that can position the engineered packaging signal at a non-wild-type location may be useful to further attenuate the packaging efficiency of the supplemental-Ad. In addition, moving the packaging signal to another place may be helpful to minimize the possibility of the reversion of the supplemental-Ad back to wild-type Ad through homologous recombination between the engineered packaging signal of the supplemental-Ad and the wild-type packaging signal of the controlled-Ad vectors.

To attenuate the packaging of the supplemental-Ad, two aspects can be considered: cis-elements and trans-acting factors. Therefore, other possible designs can be oriented towards these two aspects or any combination of these two aspects. The cis-elements are the A-repeats and the trans-acting factors are the packaging proteins. Further consideration should be a controllable mechanism of packaging without sacrificing the high titer output of the controlled-Ad vectors by the system.

3. The Controlled-Ad Vector a. The basic structure of the controlled-Ad vector Ad vectors are used as a circularized plasmid form through the fusion of ITRs (Graham, 1984). The simplest plasmid form of the controlled-Ad vectors is the circular DNA that contains an ITR fusion, plasmid DNA replication origin, the Ad E1 gene, and polycloning sites. The ITR fusion contains the left end of the wild-type Ad from map unit 0 to 1 and the right end from map unit 99 to 100, in which the DNA replication origins of Ad are located in the both ITRs and the wild-type packaging signal located next to the left ITR. The controlled-Ad vector can be controlled in two different ways: promotes replacement and functional deletion. The Ad E1-region genes with or without deletion are carried by the controlled-Ad within a specific expression cassette that has a tissue-specific or tumor-activated or other promoter/enhancer to control the E1 genes. FIG. 5 depicts the basic composition of the controlled-Ad vectors.

b. The structural and functional possibilities of the controlled-Ad vectors Based upon the basic structure of the controlled-Ad vectors, other DNA sequences and elements can be added as follows as examples:

Exression cassettes of transgenes: An expression cassette is a basic transcription unit. A simple expression cassette of a given gene is usually a linear DNA structure that consists of a promoter, the gene of interest, and a polyadenylation (polyA) signal. Within an expression cassette, two or more genes can be put to form bi- or poly-cistronic structure, as long as additional elements for translation or splicing of RNA are provided between the genes. Generally, controlled-Ad vectors can have one or multiple transgene expression cassettes.

Functional elements for vector DNA retention: Those are the elements that can help integration of the expression cassette into target cell genome or maintain the controlled-Ad vectors as an episomal form in target cells.

Regulatory elements for control of DNA transcription: Those are the elements that have transcriptional regulation function such as enhancer, repressor or activator-binding site, intron, 5' or 3'-untranslated regions, etc.

Elements for vector and transgene targeting: Targeting can be achieved at least at two levels: vector surface modification and tissue-specific expression. Tissue specific promoters can be utilized to avoid expression in any cell type but that targeted for delivery in vivo.

Other supporting elements: They can be DNA replication origins of prokaryotic or eukaryotic cells, plasmid or vector selection markers, and backbones of the vectors, etc.

c. The designs for high titer production of the controlled-Ad vectors: High-titer production of the controlled-Ad vectors is one of the major objects of this invention. One of the advantages of Ad vectors over other viral vectors is obtainable high-titer preparation of Ad vectors. The reasons for high titer propagation of Ad is mainly owing to large quantity of viral capsid protein production together with high copy number of viral genome. The followings are the examples of consideration on the methods for generating high-titer controlled-Ad vectors.

Enhanced DNA replication: Ad has its own enzymatic system for DNA replication. The E2 region proteins are the major trans-acting elements responsible for viral DNA replication. The replication origins are the cis-elements at the both ends of the viral genome. To enhance controlled-Ad genome replication, sufficient amount of E2 proteins expressed from the supplemental virus should be provided. A high-level expression of the E2 region proteins may also be achieved by adding the E2 gene into the controlled-Ad genome in addition to that in the supplemental virus. Other mechanisms for increase in copy numbers of the controlled-Ad genome will also be considered.

Enhanced packaging signal: More or better packaging sequences (either adding more tandem repeats at one end or both, or generating synthetic packaging signals).

Enhanced packaging process: The packaging process and mechanism of Ad have not been clearly understood. Whether DNA binding proteins other than the packaging signal of Ad play synergistic roles for packaging is not certain. If it is, the sequences for DNA-binding proteins, refereed to anchorage points for packaging, naturally existing in the Ad genome may need to put back to the controlled-Ad genome.

4. The Ad Helper Cell Lines

AD helper cell lines are used to provide large quantities of complementary AD vectors. Since the cell lines have trans-activation of the transcription of the AdE1 genes carried by the controlled-Ad, which in turn to activate the transcription and replication program of the supplemental-Ad genome. Different from that in 293 cells, the E1 fragment is designed to be carried by the controlled-Ad and have no overlapping sequences with the supplemental-Ad genome. The capability of the cell to activate the promoter/enhancer that controls the Ad E1 genes is critical for the cells to function as the helper cells for the complementary-Ad vectors. Other elements for genetic engineering of the helper cells are the genes for supporting high copy-number production of the controlled-Ad vector, enhancing packaging of the controlled-Ad vector, and attenuating the packaging of the supplemental-Ad.

4. The Present Invention is Particularly Useful in the Following Application:

a. To induce local tumoricidal effect and systemic anticancer immunity through intratumoral or systemic injection of the vectors: Ad vectors have a strong infectivity in cultured tumor cells and different types of solid tumor models in vivo. This characteristic of the Ad vectors has been utilized for treatment of cancer. The efficacy of treatment depends upon the oncolytic effect of the replication and propagation of the complementary-Ad in the infected tumor cells and expression of the genes that are delivered by the vectors. Multiple genes with combined functions of cytokine, chemokine, interleukin, and immuno-modulation are necessary to optimize the systemic anticancer immune responses. The complementary-Ad vectors will have the capacity to deliver multiple genes and will be useful to construct the anticancer Ad for intratumoral or systemic injection to infect cancer cells.

b. To modify in vivo target cell function or regulate target cell growth through genetic modification: Ad vectors have an advantages over other viral vectors in production of high titer viruses, which is useful for in vivo gene therapy. For treatment of epithelial or endothelial proliferating diseases such as scar tissue, prostate enlargement, vascular neointema, the complementary-Ad vectors with transiently tissue-specific suppression of the proliferating cells can be used for local application. Therefore, it will be useful for modifying in vivo target cell function or regulating target cell growth through genetic modification.

c. To specifically deliver transgenes to target cells or tissues in vivo through surface modification of the vectors: For example, the genes of hexon and fibers can be engineered to fuse with certain epitopes or ligands (e.g. the protein A that binds to Fc fragment of IgG). These modified genes can be put back to the recombinant viral genome for generation of the viruses that have surface sites to be interacted with other ligands as targeting agents. The viral particles thus produced will have tissue or cell recognition capabilities.

e. To be used for Ad-mediated vaccination via direct in vivo approaches: For the purpose of vaccination, the immunogenicity of the E1-substituted Ad vectors may be beneficial, which has been used in development of Ad-based recombinant vaccines. The contribution of the controlled-Ad vectors for this type of application will be using the E1-substituted Ad vectors as the helper virus and co-delivering genes of antigens and immuno-enhancement. Specific control of the E1 can be designed using special promoter/enhancer, such as an inducible promoter.

g. To be used as tools for basic research and development of adenovirology and novel vector construction: The complementary-Ad vector system itself has a great value for adenovirology. The construction and demonstration of the feasibility and operation are already a significant progress in the field. The supplemental-Ad and the controlled-Ad can be convenient tools for study of the Ad and its potential applications. This is particularly true for the controlled-Ad vector. The characterization of the replication, packaging, and propagation efficiency of the controlled-Ad will provide the field with important information.

h. To be used in combination with other methodology in the field of gene transfer and therapy: Ad vectors have been used together with polylysine, liposome, and other conjugation materials as a gene delivery complex. The complementary-Ad vectors can also be used in these types of combination.

i. To be used for other purposes in the field of gene transfer and therapy: The complementary-Ad vector system has a great potential to be used for gene transfer and therapy in addition to what have been discussed above. The possibilities will come across along the further development of the field of gene transfer and therapy.

EXAMPLE 1

Construction of a Controlled-Ad Vector Containing the E1 Genes Driven by the Tumor-specific α-fetoprotein (AFP) Promoter/Enhancer and Expressing Immune Modulatory Genes The present invention relates to adenoviral vectors which can be used to treat neoplasia. The vectors are made by combination of two defective vectors that complement each other and containing tumor-specific promoters driving essential viral genes. In a preferred embodiment a vector deleted in all the viral genes (controlled-Ad) and containing a α-fetoprotein promoter-E1 cassette is combined with an E1-deleted helper with a mutated packaging signal. The supplemental-Ad is deleted in the packaging signal to reduce its packaging advantage over the controlled-Ad. A supplemental-Ad (AdHβ) with a packaging signal double deletion from adenoviral nucleotides 194 to 247 and from 274 to 358 has been constructed and generated as shown in FIGS. 6 and 7.

One characteristic of hepatocellular carcinoma is that most of patients have an elevated α-fetoprotein (AFP) level in serum (Engstrom et al, 1997). This high level of AFP expression is transcriptionally controlled by the 5'-flanking sequence of the AFP gene, which occurs in hepatocellular carcinoma but not in surrounding normal liver. The specificity of AFP promoter/enhancer activation in hepatocellular carcinoma makes a specific control of Ad E1 gene possible for the complementary-Ad vector system. The present invention provides an expression cassette that has the Ad E1 genes placed downstream the 5'-flanking sequence of the AFP gene for a hepatoma-specific transcription activation. The cassette is carried by the controlled-Ad vector (pGT8025). For induction of anticancer immune response, two additional expression cassettes comprising the cDNAs encoding B7.1 co-stimulating factor and interferon-γ are included in the controlled-Ad vector.

To construct the controlled-Ad vector pGT8025, the green fluorescence protein (GFP) gene is excised from Sal I (blunt-ended)/Not I site in pAFPGFP and is replaced with E1 region excised from the Spe I (blunt-ended)/Not I site in pcE1. A Not I linker was then ligated to the Xho I site at 5′ of AFP promoter. Expression cassettes containing RSV/B7-1 and EFp/IFN-γ were then excised from pB7/IFN-γ by digestion with Pac I. The expression cassette was then cloned into the Pac I site of pGT5405 to generate pGT8026. The fragment containing the AFP/E1 expression cassette was then excised from pGT2085 using Not I and inserted into the Not I site of pGT8026 to generate the controlled-Ad vector pGT8027 (FIG. 8).

The controlled-Ad vector is then utilized to generate the "complementary-Ad" vector system by co-transfection with the supplemental-Ad DNA into a helper cell line that can activate the AFP promoter such as the HepG2 cell line. Generation of the complementary-Ad vectors may also result from transfection of the controlled-Ad vector into the helper cell line, followed by the infection of the supplemental-Ad, for rescue of the controlled-Ad. Further details provided in Example 4.

EXAMPLE 2

Construction of a Controlled-Ad Vector Containing E1 Genes Driven by H1 Autonomous Parvovirus Promoter The increased susceptibility of neoplastic cells to parvovirus-induced cytotoxicity is accompanied by an enhancement of their ability to sustain the complete parovoviral life cycle, or at least some stages of it. At the molecular level, the products of the non-structural transcription unit play a central role in this selective behavior, since malignant transformation appears to modulate the production, nuclear translocation, and activity of viral NS proteins, causing the cytotoxicity and allowing progression of the viral life cycle, i.e., DNA replication, trans-activation of the p38 promoter, and virus production. (Cornelis et al, 1990; Spegelaere et al, 1991).

On this basis of the autonomous viral biological properties (inocuousness, oncotropism, oncosuppressive activity, and ability to replicate in human cells), the rodent parvoviruses have been engineered into vector form for tumor cell targeted gene therapy (Russell et al, 1992; Dupont et al, 1994). The present invention provides a complementary-Ad vector system that includes the H1 autonomous parovoviral control elements for tumor-specific transcription activation of the Ad E1 genes is also based on the oncotropism and onco-replicative property of the virus.

Construction of a controlled-Ad vector having the Ad E1 genes under control of H1 autonomous parovoviral promoter was performed by manipulation of plasmid pH1 that contains the p4 and p38 promoters and the complete NS1 gene of H1 autonomous parvovirus (FIG. 9). A Not I linker was ligated to the Ecll36 II site of pH1 at the 3′ end of the p38 promoter. The E1 adenoviral genes were then inserted downstream of the p38 promoter at the Xba I/Not I region of pH1-Not I. Another Not I linker was then ligated to the Sal I site at 5′ end of the p4 promoter. The Not I fragment containing E1 genes under control of p4 and p38 promoter was then inserted into Not I site of pGT8026 (Example 1) to generate the controlled-Ad vector pGT8028.

For generation of the complementary-Ad with control through the H1 autonomous parovoviral promoter, the helper cells are able to utilize the p4 and p38 promoters. Many cancer cell lines or transformed cells, such as Hela, Jarket, KMMST6, MRC-5, FRE J4, U937, THP-1, and the like, can serve this purpose.

EXAMPLE 3

Variation of the Complementary-Ad Vector for Gene Therapy of Cancer and other Diseases Examples 1 and 2 demonstrate two designs for the complementary-Ad vector system, using a tissue-specific and tumor-activated promoter/enhancer to drive the Ad E1, respectively. FIG. 10 depicts other possibilities for the system. The genome of the supplemental-Ad and the controlled-Ad may include placement of Ad genes in one vector or the other such that each complements the other. The E1 gene is primarily included in the controlled-Ad genome. The complementation elements between the two vectors are listed in FIG. 10C. The transgene and supporting elements are generally included in the controlled-Ad vector, but the supplemental-Ad may also comprise such genes under certain circumstances. Deletion of an early Ad gene that encodes the cell cycling inducer will abrogate the replicative capability of adenovirus in the normal resting cells, but allow the controlled-Ad specifically drive replication and propagation of the complementary-Ad vectors in tumor cells that have defect in the counterpart of the deleted viral gene product. Two examples are the viral proteins E1b-p55 and E1b that are dispensible for virus propagation in p53-deleted (or mutated) or retinoblastoma-deleted (or mutated) tumor cells, respectively.

EXAMPLE 4

Generation and Use of the Complementary-Ad Vector for Gene Therapy of Cancer To generate the complementary-AD viral vectors, a helper cell line that is able to utilize the specific promoter of the E1 genes placed in the controlled-Ad. The present invention provides two separate complementation protocols that may be utilized and yield similar results. FIG. 11 describes the viral generation process. In the first of these methods, the controlled-Ad plasmid is co-transfected with purified supplemental-Ad DNA into a helper cell 293. Following co-transfection, the helper cells are maintained in culture until a cytopathic effect (CPE) is observed. In the second method, three days after an initial co-transfection of the controlled-Ad plasmid with a supplemental-Ad plasmid pBHG10, the host cell is infected by the supplemental-Ad (AdHβ) to rescue the controlled-Ad. The treated cells are maintained in culture until CPE appears and virus is harvested by three freeze/thaw cycles.

Following harvest of the lysate after utilization of either of the above-described methodologies, the lysate (passage 0 of the produced controlled-Ad) was used to infect a fresh monolayer of 90% confluent 293 cells (using 1 to 3 amplification scale). One day after infection, the controlled-Ad was detected under a fluorescent microscope and the presence of helper was detected by X-gal staining. If supplemental virus was present in the lysate, further incubation of the cells led to the amplification of the controlled plus supplemental mixture with the appearance of CPE (the new lysate of this monolayer will be considered as passage 1 of the minivirus). If no supplemental was present in the lysate, the controlled-Ad alone would not replicate and only by the addition of new supplemental the CPE would new virus be generated. Therefore, the presence of the supplemental-Ad may be assessed by X-gal staining and, with much higher sensitivity, by appearance of a CPE.

Following isolation of complementary Ad vectors, the viruses may be purified from cellular debris using CsCl gradients and injected locally or systemically to infect the tumor mass or the tumor bed following surgical debulking. The tumor-activated promoter/enhancer transcribes the AdE1 genes specifically in tumor cells to produce the E1A and E1B proteins that can further trans-activate the transcription and replication program of the supplemental-Ad. The controlled-Ad vector also replicates with propagation of the supplemental-Ad. Replication of the controlled-Ad produces high copy numbers of the controlled-Ad genome, which may support high level expression of the immunomodulatory genes to induce specific anti-cancer immunity. Propagation of the supplemental-Ad serves to lyse the tumor cells and further carry on the infection in neighbor cells as well as generate an immune response. The continuous local tumoricidal effect leads to a systemic antitumoral response that involves rejection of distant metastases (FIG. 12).

REFERENCES

Addison, C. L., T. Braciak, R. Ralston, W. J. Muller, J. Gauldie, and F. L. Graham. 1995. Intratumoral injection of an adenovirus expressing interleukin 2 induces regression and immunity in a murine breast cancer model. Proc. Natl. Acad. Sci. USA. 92:8522–8526.

Allione, A., M. Consalvo, P. Nanni, P. L. Lollini, F. Cavallo, M. Giovarelli, M. Forni, A. Gulino, M. P. Colombo, P. Dellabona, H. Hock, T. Blakenstein, F. M. Rosenthal, B. Gansbacher, M. C. Bosco, T. Musso, L. Gusells, and G. Forni. 1994. Immunizing and curative potential of replicating and nonreplicating murine mammary adenocarcinoma cells engineered with interleukin (IL)-2, IL-4, IL-6, IL-7, IL-10, tumor necrosis factor x, granulocyte-macrophage colony-stimulating factor, and γ-interferon gene or admixed with conventional adjuvants. Cancer Research. 54:6022–6026.

Billiau, A. 1996. Interferon-y. Biology and role in pathogenesis. Advances in immunology. 62:61–131.

Chen L. K., B. Tourvieille, G. F. Burns, F. H. Bach, D. Matieu-Mahul, M. Sasportes, and A. Bensussan. 1986. Interferon-y: a cytotoxic T-lymphocyte differentiation signal. Eur. J. Immunol. 16:767–770

Cornelis, J. J., P. Becquart, N. Duponchel, N. Salome, B. L. Avalosse, M. Namba, and J. Rommelaere. 1988. Transformation of human fibroblasts by ionizing radiation, a chemical carcinogen, or simian virus 40 correlates with an increase in susceptibility to the autonomous parvoviruses H-1 virus and minute virus of mice. J. Virol. 62:1679–1686.

Cornelis, J. J., Y. Q. Chen, N. Spruyt, N. Duponchel, S. F. Cotmore, P. Tattersall, and J. Rommelaere. 1990. Susceptibility of human cells to killing by the parvoviruses H-1 and minute virus of mice correlates with viral transcription. J. Virol. 64:2537–2544.

Crystal, R. G., N. G. McElvaney, M. A. Rosenfeld, C.-S. Chu, A. Mastrangeli, J. G. Hay, S. L. Brody, H. A. Jaffe, N. T. Eissa, and C. Danel. 1994. Administration of an adenovirus containing the human CFTR cDNA to the respiratory tract of individuals with cystic fibrosis. Nature Genetics. 8:42–51.

DiMaio, J. M., B. M. Clary, D. F. Via, E. Coveney, T. N. Pappas, and H. K. Lyerly. 1994. Directed enzyme prodrug gene therapy for pancreatic cancer in vivo. Surgery. 116:205–213.

Descamps, V., M. T. Duffour, M. C. Mathieu, N. Fernandez, L. Cordier, M. A. Abina, E. Kremer, M. Perricaudet, and H. Haddada. 1996. Strategies for cancer gene therapy using adenoviral vectors. J. Mol. Med. 74:183–189.

Dranoff, G. and R. C. Mulligan. 1995. Gene transfer as cancer therapy. Adv. in Immunol. 58:417–454.

DuPont, F., L. Tenenbaum, L. P. Guo, P. Spegelaere, M. Zeicher, and J. Rommelaere. 1994. Use of an autonomous parvovirus vector for selective transfer of a foreign gene into transformed human cells of different tissue origins and its expression therein. J. of Virology. 68:1397–1406.

Engstrom, P. F., K. McGlynn, and J. P. Hoffman. 1997. Primary neoplasms of the liver. In: Cancer Medicine (4th Edn), eds. J. F. Holland, R. C. Bast, Jr., D. L. Morton, E. Freii III, D. W. Kufe, R. R. Weichselbaum. pp. 1923–1938. Williams & Wilkins, MD Gansbacher B, Zier K, Cronin K, Hantzopoulos P A, Bouchard B, Houghton A, Gilboa, E, Golde D. 1992. Retroviral gene transfer induced constitutive expression of interleukin-2 or interferon-y in irradiated human melanoma cells. Blood. 80:2817–2825.

Gastl G, Finstad C L, Guarini A, Bosl G, Gilboa E, Bander N H, Gansbacher B. 1992. Retroviral vector-mediated lymphokine gene transfer into human renal cancer cells. Cancer Res. 52:6229–6236.

Ghosh-Choudhury, G., Y. Haj-Ahmad, P. Brinkley, J. Rudy, and F. L. Graham, F. L. 1986. Human adenovirus cloning vectors based on infectious bacterial plasmids. gene. 50:161–171.

Ghosh-Choudhury, G., Y. Hau-Ahmad, and F. L. Graham. 1987. Protein IX, a minor component of the human adenovirus capsid, is essential for the packaging of full-length genomes. EMBO J. 6:1733–1739.

Grable, M., and P. Hearing. 1992. cis and trans requirements for the selective packaging of adenovirus type 5 DNA. J. Virol. 6:723–731.

Graham, F. L. 1984. Covalently closed circles of human adenovirus DNA. EMBO J. 3:2917–2922.

Graham, F. L., and L. Prevec. 1991. Manipulation of adenovirus vectors. In: Methods in Molecular Biology (Vol. 7), Gene Transfer and Expression Protocols, ed. E. J. Murray, The Humana Press Inc., Clifton, N.J.

Graham, F. L., and L. Prevec. 1992. Adenovirus-based expression vectors and recombinant vaccines. in Vaccines. In: New Approaches to Immunological Problems Eds. R. V. Ellis. pp. 363–390. Butterworth-Heinemann, Buston.

Graham F. L., J. Smiley, W. C. Russell, and R. Nairn. 1977. Characteristics of a human cell line transformed by DNA from human adenovirus type 5. J. Gen. Virol. 36:59–72.

Grunhaus, A., and M. S. Horwitz. 1992. Adenoviruses as cloning vectors. Semin. Virol. 3:237–252.

Halbert, D. N., J. R. Cutt, and T. Shenk. 1985. Adenovirus early region 4 encodes functions required for efficient DNA replication, late gene expression, and host cell shutoff. J. Virol. 56: 250–257.

Hallenbeck, P. L., Y-N. Chang, C. Hay, D. Golightly, D. Stewart, G. McGarrity, Y. Chiang. 1996. Novel tumor specific replication competent adenoviral vectors for gene therapy of cancer. Cancer Gene Therapy. 3:S19–20.

Hart, I. 1996. Tissue specific promoters in targeting systemically delivered gene therapy. Semin. Oncol. 23:154–158.

Hearing, P., R. J. Samulsi, W. L. Wishart, and T. Shenk. 1987. Identification of a repeated sequence element required for efficient encapsidation of the adenovirus type 5 genome. J. Virol. 671:2555–2558.

Herz, J. and R. D. Gerard. 1993. Adenovirus-mediated transfer of low density lipoprotein receptor gene acutely accelerates cholesterol clearance in normal mice. Proc. Natl. Acad. Sci. USA. 90:2812–2816.

Horwitz, M. S. 1990. Adenoviridae and their replication. In: Fundamental Virology (2nd Edn), eds. B. N. Field, D. M. Knipe, R. M. Chanock, J. L. Melnick, M. S. Hirsch, T. P Monath, B. Roizman. pp. 771–813. Raven Press, N.Y.

Huber, B. E., C. A. Richards, and T. A. Krenitsky. 1991. Retroviral-mediated gene therapy for the treatment of hepatoscellular carcinoma: an innovative approach for cancer therapy. Proc. Natl. Acad. Sci. USA, 88:8039–8043.

Hui, K., F. Grosveld, and H. Festenstein. 1984. Rejection of transplantable AKR leukemia cells following MHC DNA-mediated cell transformation. Nature. 311:750–752.

Ido, A., K. Nakata, Y. Kato, K Nakao, K. Murata, M. Fujita, N. Ishii, T. Tamaoki, H. Shiku, and S. Nagataki. 1995. Gene therapy for hepatoma cells using a retrovirus vector carrying herpes simplex virus thymidine kinase gene under the control of human a-Fetoprotein gene promoter. Cancer Res. 55:3105–3109.

Kaneko, S. P. Hallenbeck, T. Kotani, H. Nakabayashi, G. McGarrity, T. Tamaoki, W. F. Anderson, and Y. L. Chiang. 1995. Adenovirus-mediate gene therapy of hepatocellular carcinoma using cancer-specific gene expression. Cancer Res. 55:5283–5287.

Le Gal La Salle, G., J. J. Robert, S. Bernard, V. Ridoux, L. D. Stratford-Perricaudet, and M. Perricaudet. 1993. An adenovirus vector for gene transfer into neurons and glia in the brain. Science. 259:988–990.

Leach, D. R., M. F. Krummel and J. P. Allison. 1996. Enhancement of antitumor immunity by CTLA-4 blockade. Science 271:1734–1736.

Lenschow, D. J., T. L. Walunas, and J. A. Bluestone. 1996. CD28/B7 system of T cell costimulation. Annu. Rev. Immunol. 14: 233–58.

Levrero, M., V. Barban, S. Manteca, A. Ballay, C. Balsamo, M. L. Avantaggiati, G. Natoli, H. Skellekens, P. Tiollais, and M. Perricaudet. 1991. Defective and nondefective adenovirus vectors for expressing foreign genes in vitro and in vivo. Gene 101: 195–202.

Manome, Y., M. Abe, M. R. Hagen, H. A. Fine, and D. W. Kufe. 1994. Enhancer sequences of the DF3 gene regulate expression of the herpes simplex virus thymidine kinase gene and confer sensitivity of human breast cancer cells to gancyclovir. Cancer Res. 54:5408–5413.

Miller, A. R., W. H. McBride, K. Hunt, and J. S. Economou. 1994. Cytokine-mediated gene therapy for cancer. Ann. of Surg. Onc. 1:436–450.

Nevins, J. R. 1993. Transcriptional activation by the adenovirus E1A proteins. Semin. Viol. 4: 25–31.

Nicholas P. R., P. J. Spiess, S. E. Karp, J. J. Mule, and S. A. Rosenberg. 1992. A nonimmunogenic sarcoma transduced with cDNA for interferon-y elicits CD8+ T cells against the wild-type tumor: correlation with antigen presentation capability. J. Exp. Med. 175:1423–1431.

Osaki, T., Y. Tanio, I. Tachibana, S. Hosoe, T. Kumagai, I. Kawase, S. Oikawa, and T. Kishimoto. 1994. Gene therapy for carcinoembryonic antigen-producing human lung cancer cells by cell type-specific expression of herpes simplex virus thymidine kinase gene. Cancer Res. 54:5258–5261.

Ostrand-Rosenberg S, Thakur A, Clements V. 1990. Rejection of mouse sarcoma cells after transfection of MHC class II gene. J. Immunol. 144:4068–4071.

Pettersson, U., and R. J. Roberts. 1986. Adenovirus gene expression and replication: a historical review. In: Cancer Cells (Vol. 4): DNA Tumor Viruses. M. Botchan, T. Glodzicker, P.A. Sharp. Eds. pp. 37–57. Cold Spring Harbor Laboratory, Cold Spring Harbor, N.Y.

Philipson, L. 1984. Adenovirus assembly. In: The Adenoviruses. ed. H. S. Ginsberg, pp. 309–337. Plenum Publishing Corp., NY.

Plata-Salaman, C. R., and J. P. Borkoski. 1994. chemokines/intercrines and central regulation of feeding. Am. J. Physiol. 266:R1711–1715.

Porgador, A., R. Bannerji, Y. Watanabe, M. Feldman, E. Gilboa, and L. Eisenbach. 1993. Antimetastatic vaccination of tumor-bearing mice with two types of IFN- γ gene-inserted tumor cells. J. Immunol. 150:1458–1470.

Quantin, B., L. D. Perricaudet, S. Tajbakhsh, and J.-L. Mandel. 1992. Adenovirus as an expression vector in muscle cells in vivo. Proc. Natl. Acad. Sci. USA. 89:2581–2584.

Rich, D. P., M. Couture, L. M. Cardoza, V. M. Guiggio, D. Armentano, P. C. Espino, K. Hehir, M. J. Welsh, A. E. Smith, and R. J. Gregory. 1993. Development and analysis of recombinant adenoviruses for gene therapy of cystic fibrosis. Human Gene Ther. 4:461–476.

Richards, C. A., E. A. Autsin, and B. E. Huber. 1995. Transcriptional regulatory sequences of carcinoembryonic antigen: identification and use with bytosine deaminase for tumor-specific gene therapy. Hum. Gene Ther. 6:881–893.

Rosenberg, S. A., M. T. Lotze, J. C. Tang, P. M. Aebersold, W. M. Linehan, C. A. Deipp, and D. E. White. 1989. Experience with the use of high-dose interleukin-2 in the treatment of 652 cancer patients. Ann. Surg. 210:474–484.

Rosenfeld, M. A., K. Yoshimura, B. C. Trapnell, K. Yoneyama, E. R. Rosenthal, W. Dalemans, M. Fukayama, J. Bargon, L. E. Stier, L. Stratford-Perricaudet, M. Perricaudet, W. B. Guggino, A. Pavirani, J.-P. Lecocq, and R. G. Crystal. 1992. In vivo transfer of the human cystic fibrosis transmembrane conductance regulator gene to the airway epithelium. Cell. 68:143–155.

Russel, S. J., A. Brandenburger, C. L. Flemming, M. K. L. Collins, and J. Rommelaere. 1992. Transformation-Dependent Expression of Interleukin Genes Delivered by a Recombinant Parvovirus. J. Virol. 66:2821–2828.

Shaw, A. R., and E. B. Ziff. 1980. Transcriptions from the adenovirus-2 major later promoter yield a single early family of 3' coterminal mRNA and five late families. Cell 22: 905–916.

Siders, W. M., P. J. halloran, and R. G. Fenton. 1996. transcriptional targeting of recombinant adenoviruses to human and murine melanoma cells. Cancer Research. 56:5638–5646.

Sinkovics, J., J. Horvath. 1993. new development in the virus therapy of cancer: a historical review. Intervirology. 36:193–214.

Smith, M. J., M. D. Rousculp, K. T. Goldsmith, D. T. Curiel, and R. I. Garver. 1994. Surfactant protein A-directed toxin gene kills lung cancer cells in vitro. Hum. Gene Ther. 5:29–35.

Smith, R. R., R. J. Huebner, W. P. Rowe, W. E. Schatten, and L. B. Thomas. 1956. Studies on the use of viruses in the treatment of carcinoma of the cervix. Cancer. 9:1211–1218.

Spegelaere, P., B. Van Hille, N. Spruyt, S. Faisst, J. J. Cornelis, and J. Rommelaere. 1991. Initiation of transcription form the minute virus of mice P4 promoter is stimulated in rat cells expressing a c-Ha-ras oncogene. J. Virol. 65:4919–4928.

Springer, T. A. 1990. Adhesion receptors of the immune system. Nature. 346:425–434.

Stratford-Perricaudet, L., and M. Perricaudet. 1991. Gene transfer into animals: the promise of adenovirus. p.

51–61, In: Human Gene Transfer, Eds, 0. Cohen-Haguenauer and M. Boiron, Editions John Libbey Eurotext, France.

Stratford-Perricaudet, L., L. Makeh, M. Perricaudet, and P. Briand. 1992. Widespread long-term gene transfer to mouse skeletal muscles and heart. J. Clin. Invest. 90: 626–630.

Sussenbach, J. S. 1984. The structure of the genome. In: The Adenoviruses. ed. H. S. Ginsberg, pp. 35–124. Plenum Publishing Corp., NY.

Townsend, S., and J. Allison. 1993. Tumor rejection after direct co-stimulation of CD8+ cells by B7-transfected melanoma cells. Science. 259:268–370.

Vagliani, M., M. Rodolfo, F. Cavallo, M. Parenza, C. Melani, G. Parmiani, G. Forni, and M. P. Colombo. 1996. Interleukin 12 potentates the curative effect of a vaccine based on interleukin 2-transduced tumor cells. Cancer Research. 56:467–470.

Vile, R. G., and I. R. Hart. 1993. In vitro and in vivo targeting of gene expression to melanoma cells. Cancer Res. 53:963–967.

Wallach, D., M. Fellous, and M. Revel. 1982. Preferential effect of interferon-y on the synthesis of HLA-antigens and their mRNAs in human cells. Nature. 299:833–836.

Wallich, R., N. Bulbuc, G. Hammerling, S. Katzav, S. Segal, and M. Feldman. 1985. Abrogation of metastatic properties of tumor cells by de novo expression of H-2K antigens following H-2 gene transfection. Nature. 315:301–305.

Wold, W. S. M., and L. R. Gooding. 1991. Region E3 of adenovirus: a cassette of genes involved in host immunosurveillance and virus-cell interactions. Virology 184: 1–8.

Zhang, J. F., C. Hu, Y. Geng, J. Selm, S. B. Klein, A. Orazi, and M. W. Taylor. 1996. Treatment of a human breast cancer xenograft with an adenovirus vector containing an interferon gene results in rapid regression due to viral oncolysis and gene therapy. Proc. Natl. Acad. Sci. USA. 93:4513–4518.

Zhang, W.-W., and X. Fang. 1995. Gene therapy strategies for cancer. Exp. Opin. Invest. Drugs 4: 487–514.

We claim:

1. An adenoviral vector for generating an infectious, replication-defective recombinant adenoviral particle comprising an adenoviral ITR, a packaging signal, and a heterologous first and second transcriptional control region, each of the transcriptional control regions being operably linked to an effector or reporter gene, at least one of the first or second transcriptional control regions being operably linked to an immunostimulatory protein, the immunostimulatory protein being IFN-γ (interferon gamma).

2. An adenoviral vector for generating an infectious, replication-defective recombinant adenoviral particle comprising an adenoviral ITR, a packaging signal, and a heterologous first, second and third transcriptional control region, each of said transcriptional control regions being operably linked to an effector or reporter gene, at least one of the first, second or third transcriptional control regions being operably linked to a gene encoding an immunostimulatory protein, the immunostimulatory protein being IFN-γ (interferon gamma).

3. The adenoviral vector illustrated in FIG. 8 termed pGT8027.

4. The adenoviral vector illustrated in FIG. 9 termed pGT8028.

* * * * *